(12) United States Patent
Kluge et al.

(10) Patent No.: US 10,611,790 B2
(45) Date of Patent: Apr. 7, 2020

(54) NICOTINAMIDE RIBOSIDE AND NICOTINAMIDE MONONUCLEOTIDE DERIVATIVES FOR USE IN THE TREATMENTS OF MITOCHONDRIAL-RELATED DISEASES

(71) Applicant: Mitobridge, Inc., Cambridge, MA (US)

(72) Inventors: Arthur Kluge, Lincoln, MA (US); Nan Ji, Arlington, MA (US)

(73) Assignee: Mitobridge, Inc., Cambridge, MA (US)

( * ) Notice: Subject to any disclaimer, the term of this patent is extended or adjusted under 35 U.S.C. 154(b) by 0 days.

(21) Appl. No.: 15/772,550

(22) PCT Filed: Nov. 2, 2016

(86) PCT No.: PCT/US2016/059984
§ 371 (c)(1),
(2) Date: May 1, 2018

(87) PCT Pub. No.: WO2017/079195
PCT Pub. Date: May 11, 2017

(65) Prior Publication Data
US 2019/0085008 A1 Mar. 21, 2019

Related U.S. Application Data

(60) Provisional application No. 62/360,766, filed on Jul. 11, 2016, provisional application No. 62/249,616, filed on Nov. 2, 2015.

(51) Int. Cl.
| | | |
|---|---|---|
| A01N 43/04 | (2006.01) | |
| A61K 31/70 | (2006.01) | |
| C07H 19/048 | (2006.01) | |

(52) U.S. Cl.
CPC .................. C07H 19/048 (2013.01)

(58) Field of Classification Search
None
See application file for complete search history.

(56) References Cited

U.S. PATENT DOCUMENTS

| | | |
|---|---|---|
| 8,575,119 B2 | 11/2013 | Wang et al. |
| 9,085,599 B2 | 7/2015 | Or et al. |

| | | | |
|---|---|---|---|
| 2007/0117765 A1 | 5/2007 | Sauve et al. | |
| 2014/0065099 A1* | 3/2014 | Alvarez | A61K 31/05 424/85.2 |
| 2016/0168184 A1* | 6/2016 | Migaud | C07H 19/048 536/28.1 |

FOREIGN PATENT DOCUMENTS

WO   2017/024255 A1   2/2017

OTHER PUBLICATIONS

Butora et al. Angew. Chem. Int. Ed. (2014), vol. 53, pp. 14046-14050.*
Cahard et al., Aryloxy phosphoramidate triesters as pro-tides. Mini Rev Med Chem. May 2004;4(4):371-81.
Felici et al., Pharmacological NAD-Boosting Strategies Improve Mitochondrial Homeostasis in Human Complex I—Mutant Fibroblasts. Mol Pharmacol. Jun. 2015;87(6):965-71.
Hecker et al., Prodrugs of phosphates and phosphonates. J Med Chem. Apr. 24, 2008;51(8):2328-45.
Yang et al., Syntheses of nicotinamide riboside and derivatives: effective agents for increasing nicotinamide adenine dinucleotide concentrations in mammalian cells. J Med Chem. Dec. 27, 2007;50(26):6458-61. Including Supporting Information.
International Search Report and Written Opinion for Application No. PCT/US2016/059984, dated Feb. 1, 2017. 13 pages.

* cited by examiner

*Primary Examiner* — Patrick T Lewis
(74) *Attorney, Agent, or Firm* — McCarter & English, LLP; Steven G. Davis; Wei Song

(57) ABSTRACT

Provided herein are compounds of Formula (I): or a pharmaceutically acceptable salt thereof, and compositions comprising such compounds that are useful for increasing the amount of NAD+ in cells. Also disclosed are methods of using the disclosed compounds and compositions for treating mitochondrial-related diseases or disorders.

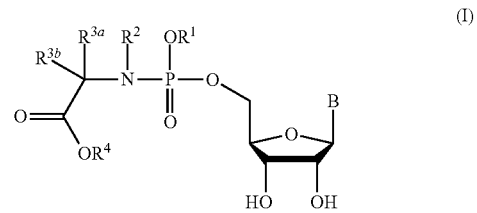

17 Claims, 2 Drawing Sheets

NICOTINAMIDE RIBOSIDE AND NICOTINAMIDE MONONUCLEOTIDE DERIVATIVES FOR USE IN THE TREATMENTS OF MITOCHONDRIAL-RELATED DISEASES

RELATED APPLICATIONS

This application is a U.S. national stage filing, under 35 U.S.C. § 371(c), of International Application No. PCT/US2016/059984, filed on Nov. 2, 2016, which claims the benefit of U.S. Provisional Application No. 62/360,766, filed on Jul. 11, 2016. This application also claims the benefit of U.S. Provisional Application No. 62/249,616, filed on Nov. 2, 2015. The entire teachings of each of the aforementioned applications are incorporated herein by reference.

FIELD

This application concerns derivatives of nicotinamide riboside (NR) and nicotinamide mononucleotide (NMN), and methods for their use, such as to treat one or more mitochondrial-related diseases.

BACKGROUND

Mitochondria are the energy centers for most eukaryotic cells. They function by converting macronutrients into energy (ATP) which cells can then use. Mitochondria have been implicated in several human diseases and disorders, including mitochondrial disorders, autoimmune disease, cancer, metabolic disease, cardiac dysfunction and heart failure, among others. Key to mitochondrial function is having enough $NAD^+$ in cells, which is used to generate energy for cells and to regulate cell functions such as signaling, immune regulation and cell death.

Mitochondrial myopathy is the term for diseases and disorders arising from damaged or defective mitochondria in cells. For most patients suffering from mitochondrial diseases, no treatments are currently available to treat the underlying deficient mitochondrial function; they are limited to treating symptoms and not the disease itself. There is still a significant unmet need for therapies which can treat mitochondria-related diseases and disorders.

SUMMARY

Provided herein are compounds and compositions comprising such compounds that are useful for increasing the amount of $NAD^+$ in cells. For example, Examples 10A and 10B demonstrate that after treatment with compounds 2-9, described herein, $NAD^+$ concentrations increase in mammalian cell lines HepG2, Huh7, and AML12. Also disclosed are methods of using the disclosed compounds and compositions for treating mitochondrial-related diseases or disorders.

Certain embodiments are compounds of Formula (I):

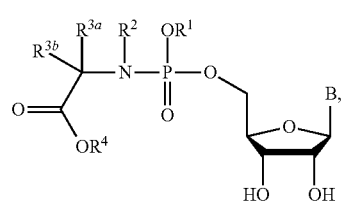

(I)

or a pharmaceutically acceptable salt thereof; wherein:
B is

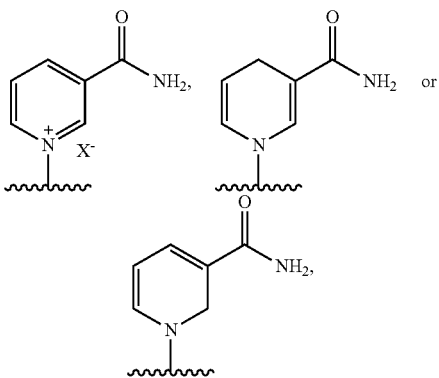

wherein $X^-$ is a counteranion; $R^1$ is phenyl optionally substituted with one or more substituents selected from halogen, hydroxyl, nitro, cyano, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy, —$N(R^{1a})_2$, $C_1$-$C_6$-acylamino, —$COR^{1b}$, —$OCOR^{1b}$, —$NHCOR^{1b}$, —$NHSO_2(C_1$-$C_6$-alkyl), —$SO_2N(R^{1a})_2$, and —$SO_2(C_1$-$C_6$-alkyl), wherein each $R^{1a}$ is independently selected from hydrogen and $C_1$-$C_6$-alkyl, and $R^{1b}$ is hydroxyl, $C_1$-$C_6$-alkoxy, $NH_2$, $NH(C_1$-$C_6$-alkyl), or $N(C_1$-$C_6$-alkyl)$_2$; $R^2$ is hydrogen or $C_1$-$C_6$-alkyl; $R^{3a}$ and $R^{3b}$ are independently hydrogen, $C_1$-$C_6$-alkyl, $C_1$-$C_6$-alkoxy, benzyl, indolyl, or imidazolyl, wherein $C_1$-$C_6$-alkyl and $C_1$-$C_6$-alkoxy can be optionally substituted with one or more of halogen, amino, amido, guanidyl, hydroxyl, thiol, and carboxyl, and benzyl can be optionally substituted with one or more halogen or hydroxyl; or $R^{3a}$ and $R^{3b}$ can be taken together with the carbon atom to which they are attached to form a $C_3$-$C_6$ cycloalkyl group optionally substituted with one or more halogen, amino, amido, guanidyl, hydroxyl, thiol, and carboxyl; and $R^4$ is hydrogen, $C_1$-$C_6$-alkyl, $C_2$-$C_6$-alkenyl, $C_2$-$C_6$-alkynyl, or $C_3$-$C_6$-cycloalkyl.

Pharmaceutical compositions of compounds of Formula (I) also are disclosed herein. Particular embodiments comprise a pharmaceutically acceptable excipient and one or more of the disclosed compounds, or a pharmaceutically acceptable salt thereof. The pharmaceutical compositions of the invention can be used in therapy, e.g., for treating a mitochondrial-related disease or condition in a subject.

Another embodiment comprises treating a mitochondrial-related disease or condition in a subject by administering to the subject a therapeutically effective amount of one or more disclosed compounds, or a pharmaceutically acceptable salt thereof, or a pharmaceutical composition comprising the compound(s).

Also provided herein is the use of one or more of the disclosed compounds, or a pharmaceutically acceptable salt thereof, or a pharmaceutical composition comprising one or more of the disclosed compounds, for the preparation of a medicament for the treatment of a mitochondrial-related disease or condition.

Another embodiment, provided herein are the disclosed compounds, or a pharmaceutically acceptable salt thereof, or a pharmaceutical composition comprising one or more of the disclosed compounds, for use in treating a mitochondrial-related disease or condition.

DETAILED DESCRIPTION

Figure 1:
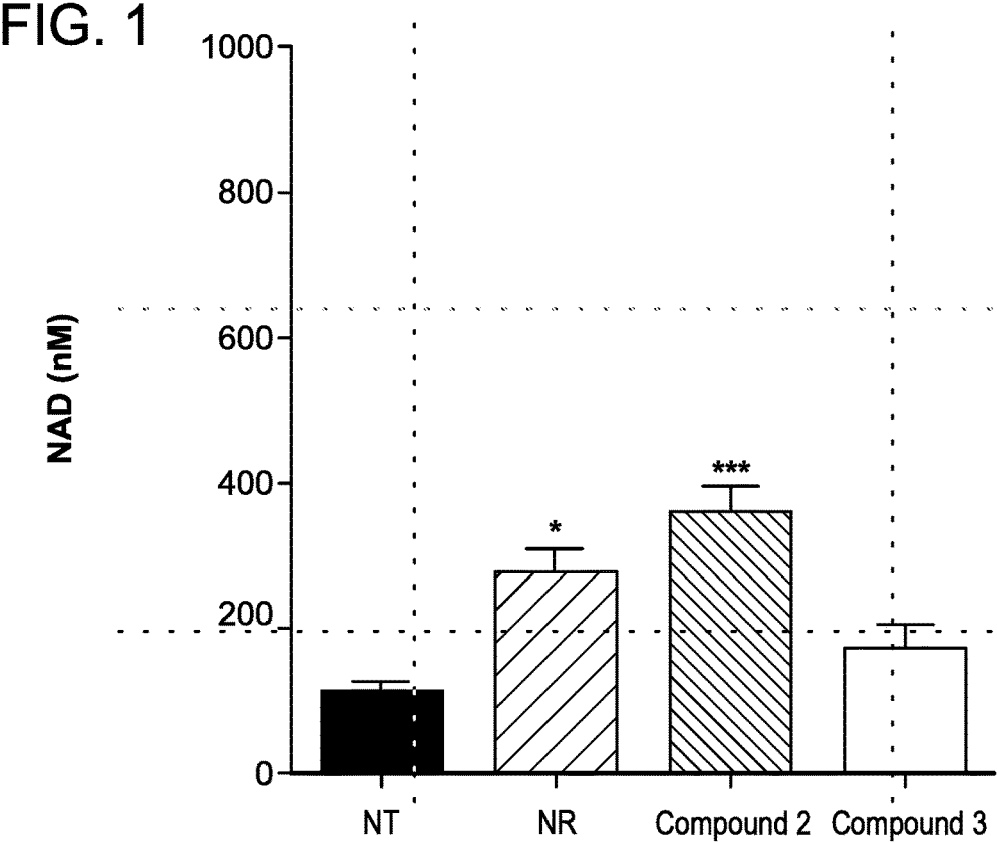
FIGS. 1 and 2 are bar graphs showing certain compounds of the invention increase $NAD^+$ levels in AML12 cells, as measured by Promega NAD-glo assay kit, wherein the cells were treated for 16 hours. See Examples 10B.

A "mitochondrial-related diseases/disorders" is characterized by malfunction of the mitochondria. A mitochondrial-related disease or disorder includes a muscle structure disorder, a neuronal activation disorder, a muscle fatigue disorder, a muscle mass disorder, a metabolic disease, a cancer, a vascular disease, an ocular vascular disease, a muscular eye disease, or a renal disease.

In some embodiments, a "mitochondrial-related disease or disorder" is selected from non-alcoholic fatty liver disease (NAFLD), non-alcoholic steatohepatitis (NASH), renal ischemia/reperfusion injury (IRI), Duchenne & Becker muscular dystrophy, diabetes (type I or type II), obesity, and sarcopenia. In another embodiment, a "mitochondrial-related disease or disorder" is selected from Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, Pearson Syndrome, platinum-based chemotherapy induced ototoxicity, Cockayne syndrome, xeroderma pigmentosum A, Wallerian degeneration, and HIV-induced lipodystrophy.

Definitions

The term "alkyl" used alone or as part of a larger moiety, such as "alkoxy", "haloalkyl", "cycloalkyl", "heterocycloalkyl", and the like, means a saturated aliphatic straight-chain or branched monovalent hydrocarbon radical. Unless otherwise specified, an alkyl group typically has 1 to 6 carbon atoms, i.e., $C_1$-$C_6$-alkyl. As used herein, a "$C_1$-$C_6$-alkyl" group is means a radical having from 1 to 6 carbon atoms in a linear or branched arrangement, such as methyl, ethyl, propyl, isopropyl, butyl, isobutyl, tert-butyl, and the like The term "alkenyl" means an unsaturated aliphatic straight-chain or branched monovalent hydrocarbon radical, containing at least one double bond. Unless otherwise specified, an alkenyl group typically has 2 to 6 carbon atoms, and can contain more than one double bond. As used herein, a "$C_2$-$C_6$-alkenyl" group is means a radical having from 2 to 6 carbon atoms in a linear or branched arrangement and one or more double bond, such as ethenyl, propenyl, butenyl, and the like.

The term "alkynyl" means an unsaturated aliphatic straight-chain or branched monovalent hydrocarbon radical, containing at least one triple bond. Unless otherwise specified, an alkynyl group typically has 2 to 6 carbon atoms, and can contain more than one triple bond. As used herein, a "$C_2$-$C_6$-alkynyl" group is means a radical having from 2 to 6 carbon atoms in a linear or branched arrangement and one or more triple bond, such as ethynyl, propynyl, butynyl, and the like.

"Alkoxy" means an alkyl radical attached through an oxygen linking atom, represented by —O-alkyl. For example, "$C_1$-$C_6$-alkoxy" includes methoxy, ethoxy, propoxy, butoxy, pentoxy, isopentoxy, isopropoxy, and hexoxy.

The terms "haloalkyl" and "haloalkoxy" mean alkyl or alkoxy, as the case may be, substituted with one or more halogen atoms. In some embodiments, "haloalkyl" and "haloalkoxy" means alkyl or alkoxy, as the case may be, substituted with one or more fluorine atoms.

The term "halogen" means fluorine or fluoro (F), chlorine or chloro (Cl), bromine or bromo (Br), or iodine or iodo (I).

The term "amino" means a —NH$_2$ group, unless otherwise specified as being substituted. The term "$C_1$-$C_6$-acylamino" means a —NHC(O)($C_1$-$C_6$-alkyl) group, wherein alkyl is as described above.

The term "amido" means a —C(O)NH$_2$ group, unless otherwise specified as being substituted.

"Cycloalkyl" means a 3-12 membered saturated aliphatic cyclic hydrocarbon radical. It can be monocyclic, bicyclic (e.g., a bridged bicyclic ring), polycyclic (e.g., tricyclic), or fused. For example, "$C_3$-$C_6$-cycloalkyl" means a radical having from 3 to 6 carbon atoms arranged in a monocyclic ring. A $C_3$-$C_6$-cycloalkyl includes, but is not limited to, cyclopropyl, cyclobutyl, cyclopentyl, and cyclohexyl.

The term "guanidyl" means a monovalent radical of guanosine, which is a nucleoside derived from guanine and ribose.

The term "counteranion" means any anion which can balance the positive charge, if present, of compounds according to formula (I), (II) and (V), such as chloride, triflate, sulfate and the like. Preferred "counteranions" include pharmaceutically acceptable anions which are suitable for administration to mammals, such as humans. Suitable pharmaceutically acceptable counteranions include inorganic anions (such as chloride, bromide, phosphate, nitrate, and sulfate) and of organic anions (such as, e.g., acetate, benzenesulfonate, benzoate, methanesulfonate, and p-toluenesulfonate). See, e.g., Bighley, et al., "Salt Forms of Drugs and Absorption" in ENCYCLOPEDIA OF PHARMACEUTICAL TECHNOLOGY, Swarbrick, J. & Boylan, J. C. (Eds.) Vol. 13, Marcel Dekker: NY (1996) p. 453-499, which is incorporated by reference in its entirety.

If a group is described as being "substituted", a non-hydrogen substituent is in the place of a hydrogen substituent on a carbon, sulfur or nitrogen of the group. Thus, for example, a substituted alkyl is an alkyl wherein at least one non-hydrogen substituent is in the place of a hydrogen substituent on the alkyl group. To illustrate, monofluoroalkyl is an alkyl substituted with a fluoro substituent, and difluoroalkyl is an alkyl substituted with two fluoro substituents. It should be recognized that if there is more than one substitution on a substituent, each non-hydrogen substituent can be identical or different (unless otherwise stated).

If a group is described as being "optionally substituted", the substituent can be either (1) not substituted, or (2) substituted.

If a group is described as being optionally substituted with up to a particular number of non-hydrogen substituents, that group can be either (1) not substituted; or (2) substituted by up to that particular number of non-hydrogen substituents or by up to the maximum number of substitutable positions on the substituent, whichever is less. Thus, for example, if a group is described as a cycloalkyl optionally substituted with up to 3 non-hydrogen substituents, then any cycloalkyl with less than 3 substitutable positions would be optionally substituted by up to only as many non-hydrogen substituents as the cycloalkyl has substitutable positions.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. The term "geometric isomer" refers to compounds having at least one double bond, wherein the double bond(s) may exist in cis (also referred to as syn or entgegen (E)) or trans (also referred to as anti or zusammen (Z)) forms as well as mixtures thereof. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer or a stereoisomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99% or 99.9% pure by weight. Geometric isomeric purity is determined by dividing the weight of the named or depicted geometric isomer in the mixture by the total weight of all of the geometric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures if one or more diastereomers e.g., racemic mixtures) of the compound.

Enantiomeric mixtures can be resolved into their component enantiomers by well-known methods, such as chiral-phase gas chromatography, chiral-phase high performance liquid chromatography, crystallizing the compound as a chiral salt complex, or crystallizing the compound in a chiral solvent. Enantiomers also can be obtained from enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers is at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. Compounds of the present teachings with basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as, e.g., acetic acid, benzenesulfonic, benzoic, methanesulfonic, and p-toluenesulfonic acids). Compounds of the present teachings with acidic groups can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

As used herein, the term "pharmaceutically-acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art. For example, S. M. Berge, et al. describes pharmacologically acceptable salts in *J. Pharm. Sci.*, 1977, 66:1-19. \

The neutral forms of the compounds of the invention are regenerated from their corresponding salts by contacting the salt with a base or acid and isolating the parent compound in the conventional manner. The parent form of the compound may differ from the various salt forms in certain physical properties, such as solubility in polar solvents. The neutral forms of compounds disclosed herein also are included in the invention.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics,* current ed.; Pergamon; and Remington's, *Pharmaceutical Sciences* (current edition), Mack Publishing Co., Easton, Pa.

As used herein, the terms "co-administration", "administered in combination with", and their grammatical equivalents, are meant to encompass administration of two or more therapeutic agents to a single subject, and are intended to include treatment regimens in which the agents are administered by the same or different route of administration, or at the same or different times. In some embodiments, the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

Compounds of the Invention

Included in the present disclosure are compounds of Formula (I) as described above. In another embodiment, are compounds according to Formula (II):

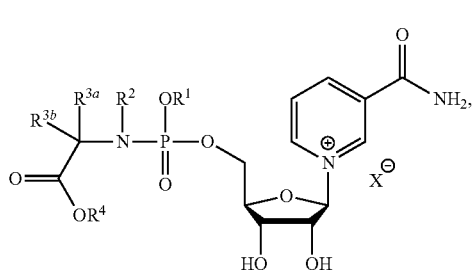

(II)

or a pharmaceutically acceptable salt thereof, wherein the definitions of the variables are as defined for the compounds of formula (I) above.

In a further aspect of the present invention, are compounds according to formula (III):

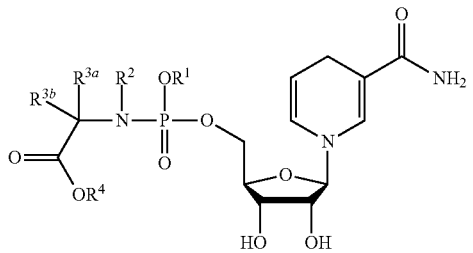

(III)

or a pharmaceutically acceptable salt thereof, wherein the definitions of the variables are as defined for the compounds of formula (I) above.

In a further aspect of the present invention, are compounds according to formula (III-A):

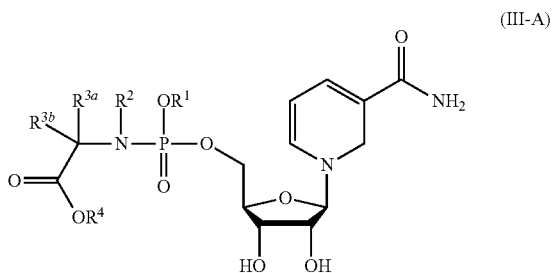

(III-A)

or a pharmaceutically acceptable salt thereof, wherein the definitions of the variables are as defined for the compounds of formula (I) above.

Another aspect of the present invention are compounds according to formula (IV) or formula (V):

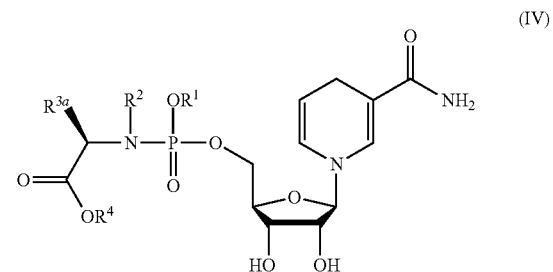

(IV)

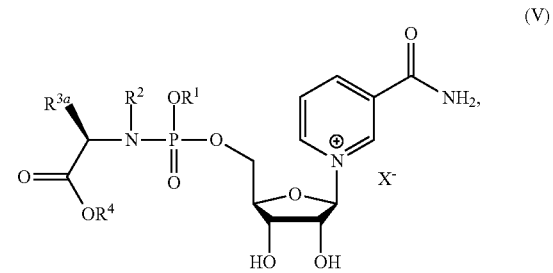

(V)

or a pharmaceutically acceptable salt thereof, wherein the definitions for $R^1$, $R^2$, $R^{3a}$ and $R^4$ are defined for formula (I) above.

Another aspect of the present invention are compounds according to formula (VI):

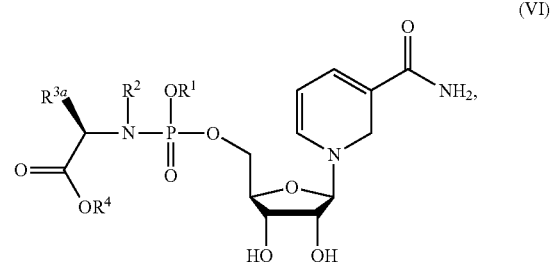

(VI)

or a pharmaceutically acceptable salt thereof, wherein the definitions for $R^1$, $R^2$, $R^{3a}$ and $R^4$ are defined for formula (I) above.

In a first specific embodiment of the invention, for any compound of formulae (I), (II), (III), (IV), (V), or (VI), $R^1$ is unsubstituted phenyl, and the remainder of the variables are as defined for formula (I) above.

In a second specific embodiment of the invention, for any compound of formulae (I), (II), (III), (IV), (V), or (VI), $R^2$ is hydrogen, and the remainder of the variables are as defined for formula (I) or for the first specific embodiment.

In a third specific embodiment of the invention, for any compound of formulae (I), (II), or (III), one of $R^{3a}$ or $R^{3b}$ is hydrogen; alternatively, for any compound of formulae (I), (II), or (III), one of $R^{3a}$ or $R^{3b}$ is optionally substituted $C_1$-$C_6$-alkyl; in another alternative of the invention, for any compound of formulae (I), (II), or (III), one of $R^{3a}$ or $R^{3b}$ is unsubstituted $C_1$-$C_6$-alkyl; and in yet another alternative, for any one of formulae (I), (II), (III), (IV), (V), or (VI), $R^{3b}$ is hydrogen and $R^{3a}$ is unsubstituted $C_1$-$C_6$-alkyl, and the remainder of the variables are as defined for formula (I), or for the first or second embodiments described above. In one aspect of any of the third specific embodiment, $R^{3a}$ is methyl.

In a fourth specific embodiment of the invention, for any compound of formulae (I), (II), or (III), $R^{3a}$ or $R^{3b}$ are taken together with the carbon atom to which they attached to form a $C_3$-$C_6$ cycloalkyl group optionally substituted with one or more halogen, amino, amido, guanidyl, hydroxyl, thiol, and carboxyl; alternatively, $R^{3a}$ or $R^{3b}$ are taken together with the carbon atom to which they attached to form an unsubstituted $C_3$-$C_6$ cycloalkyl group, and the remainder of the variables are as defined for formula (I), or for the first or second embodiments described above.

In a fifth specific embodiment of the invention, for any compound of formulae (I), (II), (III), (IV), (V), or (VI), $R^4$ is $C_1$-$C_6$-alkyl or $C_3$-$C_6$-cycloalkyl, and the remainder of the variables are as defined for formula (I), or for the first, second, third or fourth embodiments described above.

In a sixth specific embodiment, for any compound of formulae (I), (II), (III), (IV), (V), or (VI), $R^4$ is methyl, isopropyl, or cyclohexyl and the remainder of the variables are as defined for formula (I), or for the first, second, third, fourth or fifth embodiments described above.

In a seventh embodiment of the present invention, for any compound of formulae (I), (II), (III), (IV), (V), or (VI), $R^1$ is phenyl, $R^2$ is hydrogen, $R^{3a}$ is methyl, $R^{3b}$ is hydrogen, and $R^4$ is methyl, isopropyl, or cyclohexyl.

In certain embodiments, the invention is any one of the compounds depicted in the exemplification section of the instant application; pharmaceutically acceptable salts as well as the neutral forms of these compounds also are included in the invention. Specifically, the invention is any one of the compounds depicted in Examples 1-4; pharmaceutically acceptable salts as well as the neutral forms of these compounds also are included in the invention. In preferred embodiments, the invention is any one of Compounds 1-9, shown below in Table I; a pharmaceutically acceptable salt thereof, as well as the neutral form of this compound are also included in the invention.

TABLE I

Compounds of the Invention

Compound 1

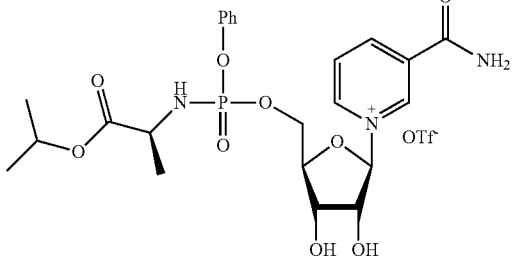

Compound 2

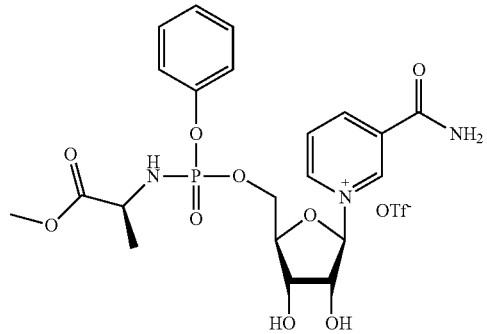

TABLE I-continued
Compounds of the Invention
Compound 3
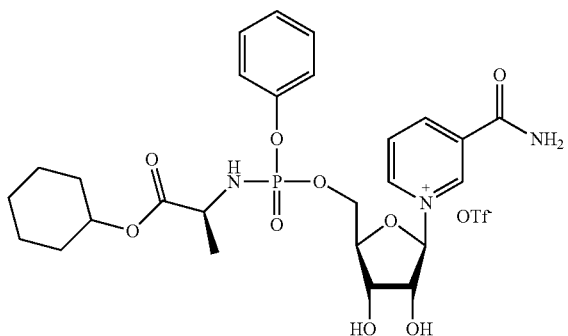
Compound 4
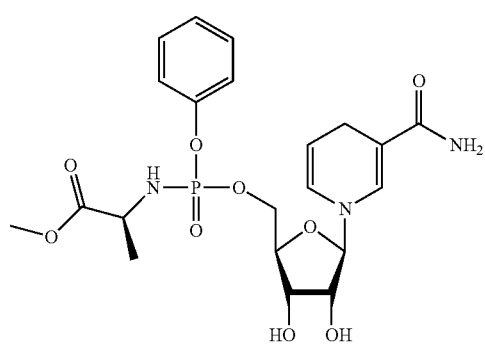
Compound 5
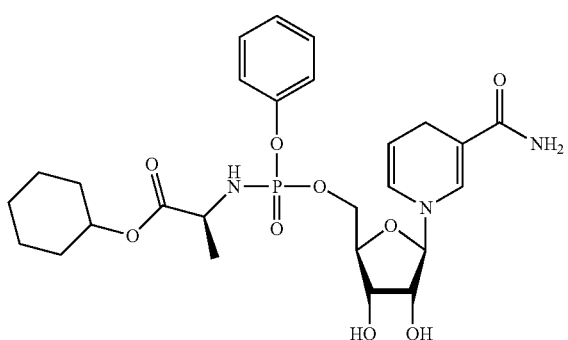
Compound 6
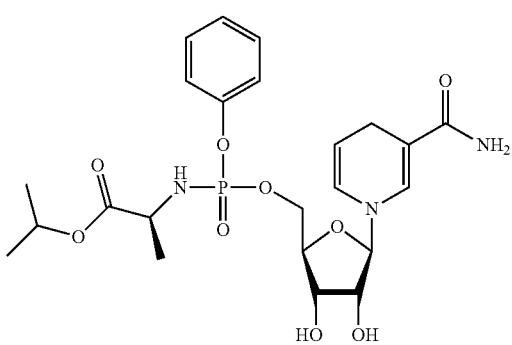
Compound 7
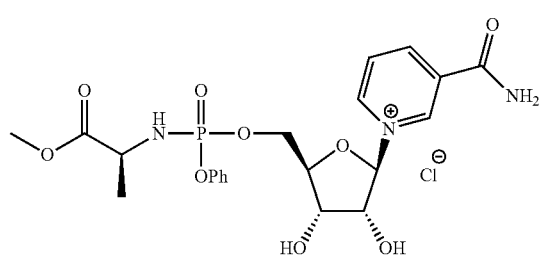 [SMILES: COC(=O)[C@H](C)NP(=O)(OC[C@H]1O[C@@H]([n+]2cccc(C(N)=O)c2)[C@H](O)[C@@H]1O)Oc1ccccc1 ; [Cl-]]

TABLE I-continued

Compounds of the Invention

Compound 8

[Chemical structure of Compound 8]

Compound 9

[Chemical structure of Compound 9]

Methods of Treatment

Methods of treating a mitochondria-related disease or condition in a subject are disclosed. The methods can include administering to the subject a therapeutically effective amount of one or more compounds or compositions provided herein.

In one embodiment, the mitochondrial-related disease or disorder includes, but is not limited to, Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, Pearson Syndrome, platinum-based chemotherapy induced ototoxicity, Cockayne syndrome, xeroderma pigmentosum A, Wallerian degeneration, and HIV-induced lipodystrophy.

In one embodiment, the mitochondrial-related disease or disorder is a muscle structure disorder, a neuronal activation disorder, a muscle fatigue disorder, a muscle mass disorder, a metabolic disease, a cancer, a vascular disease, an ocular vascular disease, a muscular eye disease, or a renal disease.

In one aspect of this embodiment, the muscle structure disorder is selected from Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, or stress urinary incontinence.

In another aspect of the embodiment, the neuronal activation disorder is selected from amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In another aspect of this embodiment, the muscle fatigue disorder is selected from chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, or thyrotoxic myopathy; the muscle mass disorder is cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In another aspect of this embodiment, the beta oxidation disease is selected from systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of β-oxidation (RR-MADD).

In yet another aspect of this embodiment, the metabolic disease is selected from hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, Non-alcoholic fatty liver disease (NAFLD), Nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In another aspect of this embodiment, the vascular disease is selected from peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In another aspect of this embodiment, the ocular vascular disease is selected from age-related macular degeneration (AMD), stargardt disease, hypertensive retinopathy, diabetic retinopathy, retinopathy, macular degeneration, retinal haemorrhage, and glaucoma.

In a further aspect of this embodiment, the muscular eye disease is selected from strabismus, progressive external ophthalmoplegia, esotropia, exotropia, a disorder of refraction and accommodation, hypermetropia, myopia, astigmatism, anisometropia, presbyopia, a disorders of accommodation, and internal ophthalmoplegia.

In a final aspect of this embodiment, the renal disease is selected from glomerulonephritis, glomerulosclerosis, nephrotic syndrome, hypertensive nephrosclerosis, acute nephritis, recurrent hematuria, persistent hematuria, chronic nephritis, rapidly progressive nephritis, acute renal failure (also known as acute kidney injury), chronic renal failure, diabetic nephropathy, and Bartter's syndrome.

In still another embodiment, the mitochondrial-related disease is cancer. Examples of cancer include, but are not limited to, cancers of the colon, large intestine, skin, breast, prostate, ovary, and/or lung.

In a final embodiment, the mitochondrial-related disease or condition is selected from genetic lipodystrophy, non-alcoholic fatty liver disease (NAFLD), non-alcoholic steatohepatitis (NASH), renal ischemia/reperfusion injury (IRI), Duchenne & Becker muscular dystrophy, diabetes (type I or type II), obesity, and sarcopenia.

Also disclosed herein are methods of treating a disease or disorder that would benefit from increased $NAD^+$ levels, for example by increasing in vivo levels of $NAD^+$ (e.g. intracellular $NAD^+$ levels, levels of $NAD^+$ in tissues or plasma, and/or overall $NAD^+$ levels in an organism).

In certain embodiments, the invention provides methods for using the compounds of the invention and pharmaceutical compositions thereof. The compounds of the invention and pharmaceutical compositions thereof may be useful for a variety of therapeutic applications including, for example, treating and/or reducing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of one or more compounds of the invention and/or pharmaceutical compositions thereof.

In another embodiment, the compounds of the invention and pharmaceutical compositions thereof may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated using the compounds of the invention and pharmaceutical compositions thereof prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with the nicotinamide riboside chloride preparations or pharmaceutical compositions of the invention, or may have a subset of cells/tissue treated locally with the compounds of the invention and pharmaceutical compositions thereof. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, the compounds of the invention and/or a pharmaceutical composition thereof can be used to treat skin conditions. Exemplary skin conditions that may be treated in accordance with the methods described herein include disorders or diseases associated with or caused by inflammation, sun damage or natural aging. For example, the compositions find utility in the treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, the compounds of the invention and pharmaceutical compositions thereof may be used for the treatment of wounds and/or burns to promote healing, including, for example, first-, second- or third-degree burns and/or thermal, chemical or electrical burns.

The compounds of the invention and pharmaceutical compositions thereof can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

The compounds of the invention and pharmaceutical compositions thereof can also be administered to a subject suffering from an acute disease, e.g., damage to an organ or tissue, e.g., a subject suffering from stroke or myocardial infarction or a subject suffering from a spinal cord injury. The compounds of the invention and pharmaceutical compositions thereof may also be used to repair an alcoholic's liver.

In another embodiment, the invention provides a method for treating a cardiovascular disease by administering to a subject in need thereof one or more of the compounds of the invention and/or a pharmaceutical composition thereof. Cardiovascular diseases that can be treated using the compounds of the invention and pharmaceutical compositions thereof include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated include those related to platelet aggregation, the retinal arterioles, the glomerular arterioles, the vasa nervorum, cardiac arterioles, and associated capillary beds of the eye, the kidney, the heart, and the central and peripheral nervous systems. The compounds of the invention and pharmaceutical compositions thereof may also be used for increasing HDL levels in plasma of an individual.

The compounds of the invention and pharmaceutical compositions thereof may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the compound is administered as a prophylactic measure. In another embodiment, the radiation or toxin exposure is received unintentionally, e.g., as a result of an industrial accident, habitation in a location of natural radiation, terrorist act, or act of war involving radioactive or toxic material. In such a case, the compounds of the invention and pharmaceutical compositions thereof is preferably administered as soon as possible after the exposure to inhibit apoptosis and the subsequent development of acute radiation syndrome.

In another embodiment, the compounds of the invention and pharmaceutical compositions thereof may be useful for treating age-related disorders, such as, for example, cancer. Exemplary cancers that may be treated using the compounds of the invention and pharmaceutical compositions thereof include those of the brain and kidney; hormone-dependent cancers including breast, prostate, testicular, and ovarian cancers; lymphomas, and leukemias. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of one or more of the compounds of the invention and pharmaceutical compositions thereof.

In certain aspects, the compounds of the invention and pharmaceutical compositions thereof can be used to treat patients suffering from neurodegenerative diseases, and traumatic or mechanical injury to the central nervous system (CNS) or peripheral nervous system (PNS). Examples of neurodegenerative diseases include, but are not limited to, Alzheimer's disease (AD), Parkinson's disease (PD), Huntington disease (HD), amyotrophic lateral sclerosis (ALS; Lou Gehrig's disease), diffuse Lewy body disease, choreaacanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. The compounds of the invention and pharmaceutical compositions thereof can be used to treat these disorders and others as described below.

In an exemplary embodiment, the compounds of the invention and pharmaceutical compositions thereof may be used to treat multiple sclerosis (MS), including relapsing MS and monosymptomatic MS, and other demyelinating conditions, such as, for example, chromic inflammatory demyelinating polyneuropathy (CIDP), or symptoms associated therewith.

In yet another embodiment, the compounds of the invention and pharmaceutical compositions thereof may be used to treat trauma to the nerves, including, trauma due to disease, injury (including surgical intervention), or environmental trauma (e.g., neurotoxins, alcoholism, etc.).

The compounds of the invention and pharmaceutical compositions thereof may also be useful to treat and alleviate symptoms of various peripheral nervous system (PNS) disorders. PNS disorders include a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used. PNS disorders may be the result of, for example, leprosy, diabetes, Guillain-Barre syndrome, and others.

Other PNS diseases treatable with the compounds of the invention and pharmaceutical compositions thereof include: Brachial Plexus Neuropathies (diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions. See Adams et al., *Principles of Neurology*, 6th ed. pp. 1351-2); Diabetic Neuropathies (peripheral, autonomic, and cranial nerve disorders that are associated with diabetes mellitus). These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy (see Adams et al., *Principles of Neurology*, 6th ed., p. 1325); mononeuropathies (disease or trauma involving a single peripheral nerve in isolation, or out of proportion to evidence of diffuse peripheral nerve dysfunction). Mononeuropathy multiplex refers to a condition characterized by multiple isolated nerve injuries. Mononeuropathies may result from a wide variety of causes, including ischemia; traumatic injury; compression; connective tissue diseases; cumulative trauma disorders; and other conditions; Neuralgia (intense or aching pain that occurs along the course or distribution of a peripheral or cranial nerve); Peripheral Nervous System Neoplasms (neoplasms which arise from peripheral nerve tissue). This includes neurofibromas; Schwannomas; granular cell tumors; and malignant peripheral nerve sheath tumors. See DeVita Jr et al., Cancer: Principles and Practice of Oncology, 5th ed, pp 1750-1); and Nerve Compression Syndromes (mechanical compression of nerves or nerve roots from internal or external causes). These may result in a conduction block to nerve impulses, due to, for example, myelin sheath dysfunction, or axonal loss. The nerve and nerve sheath injuries may be caused by ischemia; inflammation; or a direct mechanical effect; Neuritis (a general term indicating inflammation of a peripheral or cranial nerve). Clinical manifestation may include pain; paresthesias; paresis; or hyperthesia; Polyneuropathies (diseases of multiple peripheral nerves). The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance.

The compounds of the invention and pharmaceutical compositions thereof can also be used to treat blood coagulation disorders (or hemostatic disorders). As used interchangeably herein, the terms "hemo stasis", "blood coagulation," and "blood clotting" refer to the control of bleeding, including the physiological properties of vasoconstriction and coagulation.

The present invention also provides anticoagulation and antithrombotic treatments aiming at inhibiting the formation of blood clots in order to treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering the compounds of the invention and pharmaceutical compositions thereof. The compositions and methods disclosed herein are useful for the treatment of thrombotic disorders. As used herein, the term "thrombotic disorder" includes any disorder or condition characterized by excessive or unwanted coagulation or hemostatic activity, or a hypercoagulable state. Examples of thrombotic disorders include, but are not limited to, thromboembolism, deep vein thrombosis, pulmonary embolism, stroke, myocardial infarction, miscarriage, thrombophilia associated with anti-thrombin III deficiency, protein C deficiency, protein S deficiency, resistance to activated protein C, dysfibrinogenemia, fibrinolytic disorders, homocystinuria, pregnancy, inflammatory disorders, myeloproliferative disorders, arteriosclerosis, angina, e.g., unstable angina, disseminated intravascular coagulation, thrombotic thrombocytopenic purpura, cancer metastasis, sickle cell disease, glomerular nephritis, and drug induced thrombocytopenia (including, for example, heparin induced thrombocytopenia).

In addition, the compounds of the invention and pharmaceutical compositions thereof may be administered to reduce thrombotic events or to reduce re-occlusion during or after therapeutic clot lysis or procedures such as angioplasty or surgery.

The compounds of the invention and pharmaceutical compositions thereof may also be used for treating or reducing weight gain or obesity in a subject. For example, the compounds of the invention and pharmaceutical compositions thereof may be used, for example, to treat hereditary obesity, dietary obesity, hormone related obesity, obesity related to the administration of medication, to reduce the weight of a subject, or to reduce weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, the compounds of the invention and pharmaceutical compositions thereof may be administered to subjects suffering from a variety of other diseases and conditions that may be treated by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self-esteem). Stunkard A J, Wadden T A. (Editors) Obesity: theory and therapy, Second Edition. New York: Raven Press, 1993. Finally, patients with AIDS can develop lipodystrophy or insulin resistance in response to combination therapies for AIDS. In another embodiment, the compounds of the invention and pharmaceutical compositions thereof may be used for inhibiting adipogenesis or fat cell differentiation, whether in vitro or in vivo. In particular, high circulating levels of insulin and/or insulin like growth factor (IGF) 1 will be prevented from recruiting preadipocytes to differentiate into adipocytes. Such methods may be used for treating obesity.

In other embodiments, the compounds of the invention and pharmaceutical compositions thereof may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In other embodiments, the compounds of the invention and pharmaceutical compositions thereof may be used to treat a subject who has cachexia or may be likely to develop cachexia. A method may further comprise monitoring in the subject the state of the disease. Methods for promoting appetite and/or weight gain may include, for example, prior identifying a subject as being in need of decreased fat or lipid metabolism, e.g., by weighing the subject, determining the BMI of the subject. The method may also include monitoring the subject, e.g., during and/or after administration of the compounds of the invention and pharmaceutical compositions thereof. The administering can include one or more dosages, e.g., delivered in boluses or continuously. Monitoring can include evaluating a hormone or a metabolite. Exemplary hormones include leptin, adiponectin, resistin, and insulin. Exemplary metabolites include triglycerides, cholesterol, and fatty acids.

In another embodiment, the compounds of the invention and pharmaceutical compositions thereof may be administered to reduce drug-induced weight gain. For example, the compounds of the invention and pharmaceutical compositions thereof may be administered as a combination therapy with medications that may stimulate appetite or cause weight gain, in particular, weight gain due to factors other than water retention.

Examples of medications that may cause weight gain, include for example, diabetes treatments, including, for example, sulfonylureas (such as glipizide and glyburide), thiazolidinediones (such as pioglitazone and rosiglitazone), meglitinides, nateglinide, repaglinide, sulphonylurea medicines, and insulin; anti-depressants, including, for example, tricyclic antidepressants (such as amitriptyline and imipramine), irreversible monoamine oxidase inhibitors (MAOIs), selective serotonin reuptake inhibitors (SSRIs), bupropion, paroxetine, and mirtazapine; steroids, such as, for example, prednisone; hormone therapy; lithium carbonate; valproic acid; carbamazepine; chlorpromazine; thiothixene; beta blockers (such as propranolol); alpha blockers (such as clonidine, prazosin and terazosin); and contraceptives including oral contraceptives (birth control pills) or other contraceptives containing estrogen and/or progesterone (Depo-Provera, Norplant, Ortho), testosterone or Megestrol. In another exemplary embodiment, the compounds of the invention and pharmaceutical compositions thereof may be administered as part of a smoking cessation program to reduce weight gain or reduce weight already gained.

In another aspect, the compounds of the invention and pharmaceutical compositions thereof may be used for treating a metabolic disorder, such as insulin-resistance, a pre-diabetic state, type II diabetes, and/or complications thereof.

Administration of the compounds of the invention and pharmaceutical compositions thereof may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

The compounds of the invention and pharmaceutical compositions thereof can also be used to treat a disease or disorder associated with inflammation. The compounds of the invention and pharmaceutical compositions thereof. Exemplary inflammatory conditions include, for example, multiple sclerosis, rheumatoid arthritis, psoriatic arthritis, degenerative joint disease, spondouloarthropathies, gouty arthritis, systemic lupus erythematosus, juvenile arthritis, rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatitis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, scleroderma, psoriasis, and dermatosis with acute inflammatory components.

In another embodiment, the compounds of the invention and pharmaceutical compositions thereof the compounds of the invention and pharmaceutical compositions thereof may be used to treat allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, the compounds of the invention and pharmaceutical compositions thereof may be used to treat autoimmune diseases and/or inflammation associated with autoimmune diseases such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosus, Addison's disease, autoimmune polyglandular disease (also known as autoimmune polyglandular syndrome), and Grave's disease.

The compounds of the invention and pharmaceutical compositions thereof may also be used for reducing the incidence or severity of flushing and/or hot flashes which are symptoms of a disorder. In one embodiment, the compounds of the invention and pharmaceutical compositions thereof may be used to reduce flushing side effects of a vasodilator or an antilipemic agent (including anticholesteremic agents and lipotropic agents). In an exemplary embodiment, a nicotinamide riboside chloride preparation or pharmaceutical composition of the invention.

In another representative embodiment, the method involves the use of the compounds of the invention and pharmaceutical compositions thereof to reduce flushing side effects of antidepressants or anti-psychotic agent. For instance, the compounds of the invention and pharmaceutical compositions thereof can be used in conjunction (administered separately or together) with a serotonin reuptake inhibitor, a 5HT2 receptor antagonist, an anticonvulsant, a norepinephrine reuptake inhibitor, an alpha-adrenoreceptor antagonist, an NK-3 antagonist, an NK-1 receptor antagonist, a PDE4 inhibitor, an Neuropeptide Y5 Receptor Antagonists, a D4 receptor antagonist, a 5HT1 A receptor antagonist, a 5HT1D receptor antagonist, a CRF antagonist, a monoamine oxidase inhibitor, or a sedative-hypnotic drug.

In certain embodiments, the compounds of the invention and pharmaceutical compositions thereof may be used as part of a treatment with a serotonin reuptake inhibitor (SRI) to reduce flushing. In certain preferred embodiments, the SRI is a selective serotonin reuptake inhibitor (SSRI), such as a fluoxetinoid (fluoxetine, norfluoxetine) or a nefazodonoid (nefazodone, hydroxynefazodone, oxonefazodone). Other exemplary SSRI's include duloxetine, venlafaxine, milnacipran, citalopram, fluvoxamine, paroxetine and sertraline. The compounds of the invention and pharmaceutical compositions thereof can also be used as part of a treatment with sedative-hypnotic drug, such as selected from the group consisting of a benzodiazepine (such as alprazolam, chlordiazepoxide, clonazepam, chlorazepate, clobazam, diazepam, halazepam, lorazepam, oxazepam and prazepam), Zolpidem, and barbiturates. In still other embodiments, the compounds of the invention and pharmaceutical compositions thereof may be used as part of a treatment with a 5-HT1 A receptor partial agonist, such as selected from the group consisting of buspirone, flesinoxan, gepirone and ipsapirone. The compounds of the invention and pharmaceutical compositions thereof can also be used as part of a treatment with a norepinephrine reuptake inhibitor, such as selected from tertiary amine tricyclics and secondary amine tricyclics. Exemplary tertiary amine tricyclics include amitriptyline, clomipramine, doxepin, imipramine and trimipramine. Exemplary secondary amine tricyclics include amoxapine, desipramine, maprotiline, nortriptyline and protriptyline. In certain embodiments, the compounds of the invention and pharmaceutical compositions thereof may be used as part of a treatment with a monoamine oxidase inhibitor, such as selected from the group consisting of isocarboxazid, phenelzine, tranylcypromine, selegiline and moclobemide.

In still another representative embodiment, the compounds of the invention and pharmaceutical compositions thereof may be used to reduce flushing side effects of chemotherapeutic agents, such as cyclophosphamide, and tamoxifen.

In another embodiment, the compounds of the invention and pharmaceutical compositions thereof may be used to reduce flushing side effects of calcium channel blockers, such as amlodipine.

In another embodiment, the compounds of the invention and pharmaceutical compositions thereof may be used to reduce flushing side effects of antibiotics. For example, the compounds of the invention and pharmaceutical compositions thereof can be used in combination with levofloxacin. Levofloxacin is used to treat infections of the sinuses, skin, lungs, ears, airways, bones, and joints caused by susceptible bacteria.

The compounds of the invention and pharmaceutical compositions thereof may be used for treating viral infections (such as infections by influenza, herpes or papilloma virus) or as antifungal agents.

Pharmaceutical Compositions and Administration Thereof
Additional Therapeutic Agents Pharmaceutical compositions are disclosed that include one or more compounds provided herein (such as 1, 2, 3, 4 or 5 of such compounds), and typically at least one additional substance, such as an excipient, a known therapeutic other than those of the present disclosure, and combinations thereof. In some embodiments, the disclosed compounds can be used in combination with other agents known to have beneficial activity targeting diseases or disorders listed above. For example, disclosed compounds can be administered alone or in combination with one or more compounds selected from the group consisting of: PPAR δ agonists, AMPK activators, PARP inhibitors, SIRT-activating compounds, and acetyl-CoA carboxylase inhibitors, and the pharmaceutically acceptable salts of these compounds.

In one embodiment, disclosed compounds may be administered in combination with dexamphetamine, amphetamine, mazindole or phentermine; and administered in combination with medicaments having an anti-inflammatory effect.

Further, when used for the treatment of a metabolic condition, the pharmaceutical compositions provided herein can be administered as a combination therapy with one or more pharmacologically active substances having favorable effects on metabolic disturbances or disorders. For example, the disclosed pharmaceutical compositions may be administered in combination with RXR agonists for treating metabolic and cardiovascular diseases medicaments, which lower blood glucose; antidiabetics, such as insulins and insulin derivatives, including Lantus, Apidra, and other fast-acting insulins, and GLP-1 receptor modulators; active ingredients for treating dyslipidemias; anti-atherosclerotic medicaments; anti-obesity agents; anti-inflammatory active ingredients; active ingredients for treating malignant tumors; anti-thrombotic active ingredients; active ingredients for treating high blood pressure; active ingredients for treating heart failure, and combinations thereof.

Methods of Administration

The precise amount of compound administered to provide an "therapeutically effective amount" to the subject will depend on the mode of administration, the type, and severity of the cancer, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used by following, for example, dosages reported in the literature and recommended in the *Physician's Desk Reference* (57th ed., 2003).

The term "therapeutically effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a mitochondria-related disease using the disclosed compounds for guidance.

The disclosed compound of Formula (I, II, III, IV or V) can be administered to a subject by routes known to one of skill in the art. Examples of routes of administration include, but are not limited to, parenteral, e.g., intravenous, intradermal, subcutaneous, oral, intranasal (e.g., inhalation), transdermal, topical, transmucosal, and rectal administration.

Pharmaceutical compositions are disclosed that include the compound of Formula (I, II, III, IV or V)), and typically at least one additional substance, such as an excipient, a known therapeutic other than those of the present disclosure, and combinations thereof.

The pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration. Pharmaceutically acceptable formulations of the compound of Formula (I, II, III, IV or V), and the preparations thereof, can be found in PCT Patent Publication No. WO 2015/186068, incorporated herein by reference.

General Synthesis

Compounds according to formula (I) can be synthesized using the methodology shown in Schemes 1 and 2.

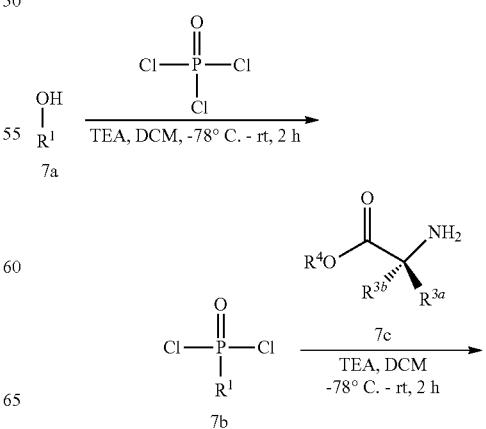

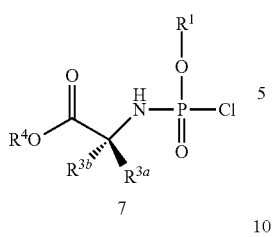

Phosphoryl chloride can be converted to the corresponding phosphate ester by reacting it with about 1 equivalent of an alcohol (7a), preferably in the presence of an HCl acceptor, such as pyridine or an amine, such as triethylamine, which isn't strongly nucleophilic. The phosphonate ester (7b) can then be reacted with the substituted amine shown above, typically in the presence of a base such as triethylamine to yield compound (7).

Scheme 2

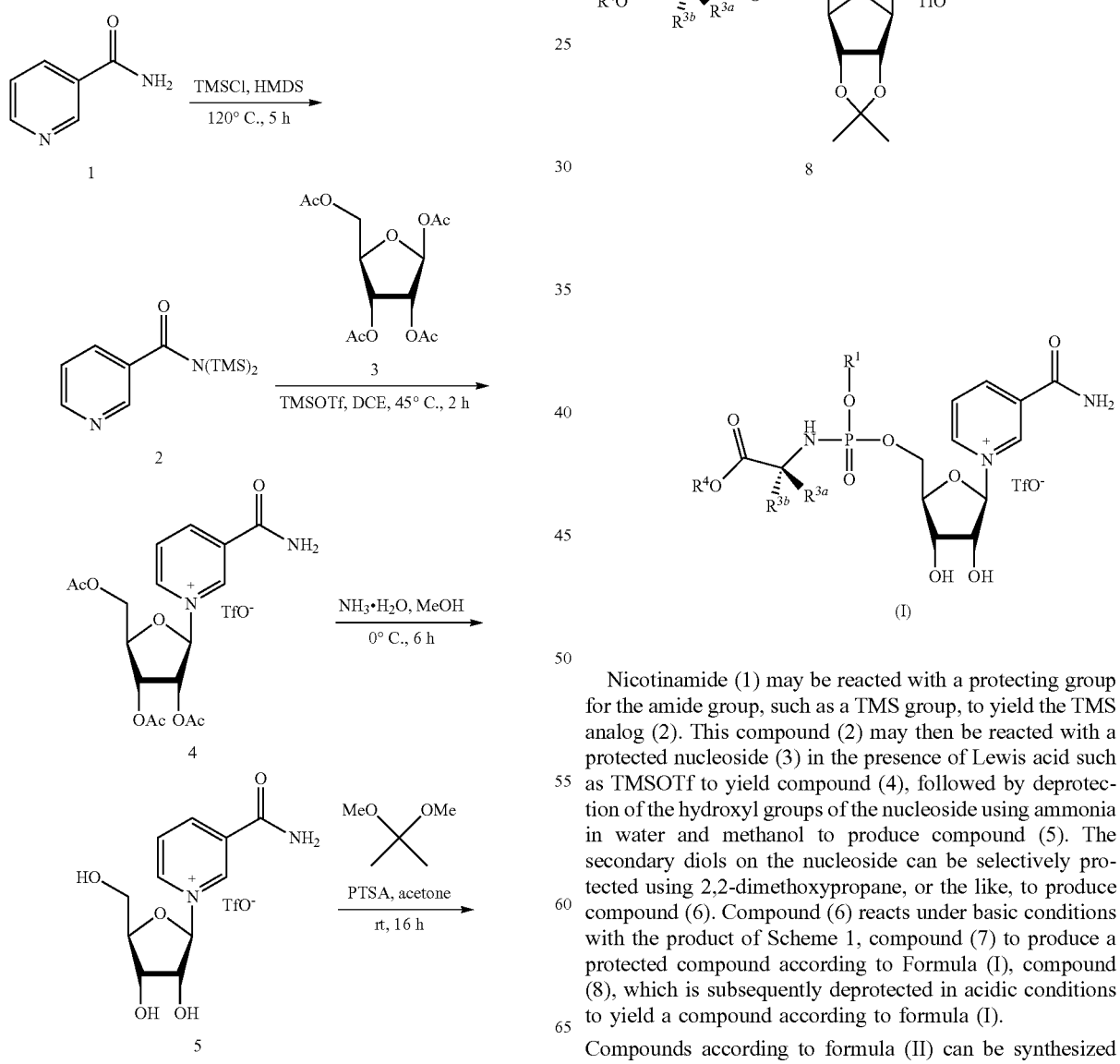

Nicotinamide (1) may be reacted with a protecting group for the amide group, such as a TMS group, to yield the TMS analog (2). This compound (2) may then be reacted with a protected nucleoside (3) in the presence of Lewis acid such as TMSOTf to yield compound (4), followed by deprotection of the hydroxyl groups of the nucleoside using ammonia in water and methanol to produce compound (5). The secondary diols on the nucleoside can be selectively protected using 2,2-dimethoxypropane, or the like, to produce compound (6). Compound (6) reacts under basic conditions with the product of Scheme 1, compound (7) to produce a protected compound according to Formula (I), compound (8), which is subsequently deprotected in acidic conditions to yield a compound according to formula (I).

Compounds according to formula (II) can be synthesized using the methodology shown in Schemes 1, 2 and 3.

Scheme 3

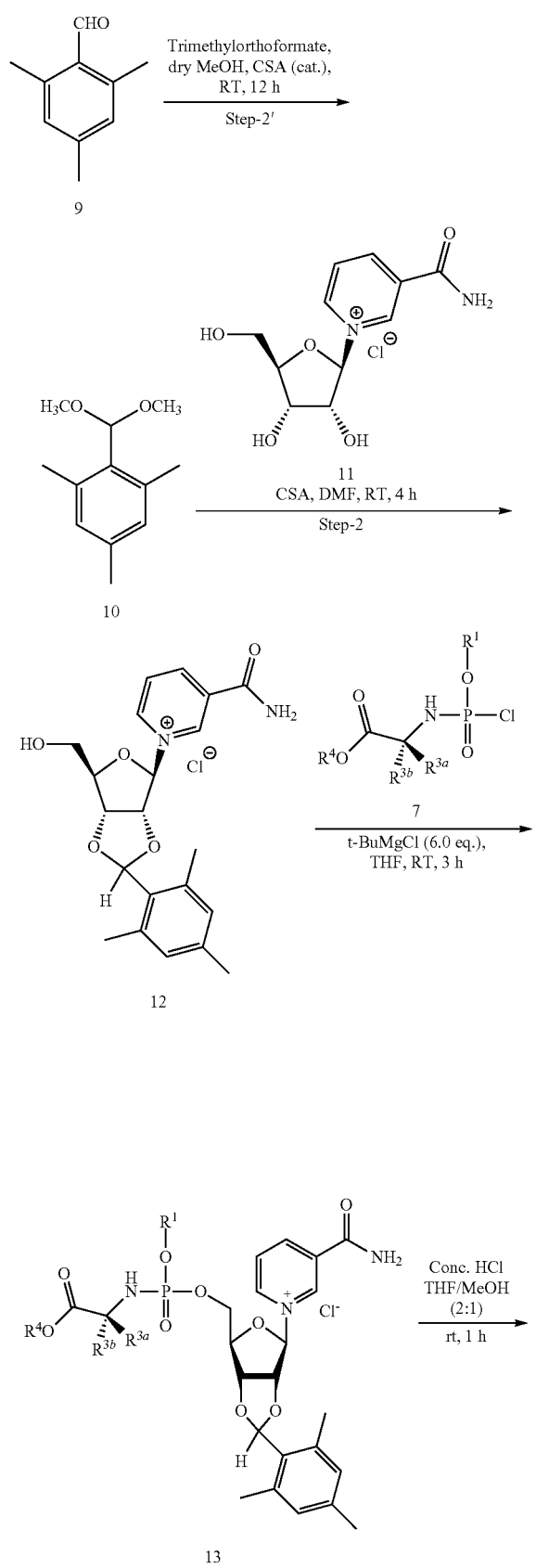

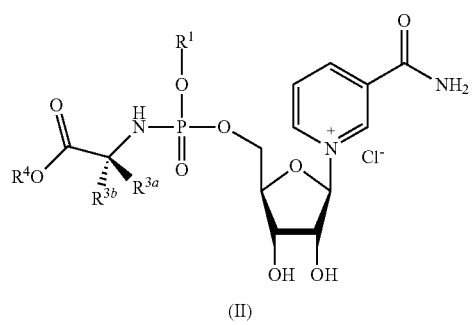

(II)

Mesitaldehyde (9) may be reacted with trimethylorthoformate to yield the dimethylacetal (10). This compound (10) may then be reacted with nicotinamide riboside (11) in the presence of Lewis acid such as CSA to yield compound 12, followed by coupling of the hydroxyl groups of the nucleoside under basic conditions with the product of Scheme 1, compound 7 to produce a protected compound according to Formula (II), compound 13, which is subsequently deprotected in acidic conditions to yield a compound according to formula (II).

Compounds according to formula (III) can be synthesized using the methodology shown in Schemes 1, 2, and 4.

Scheme 4

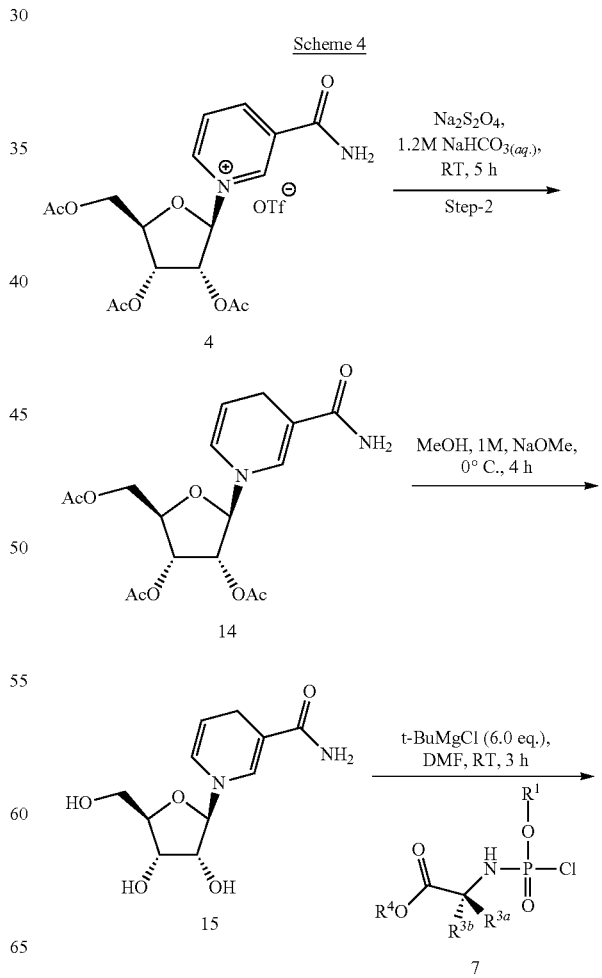

29

-continued

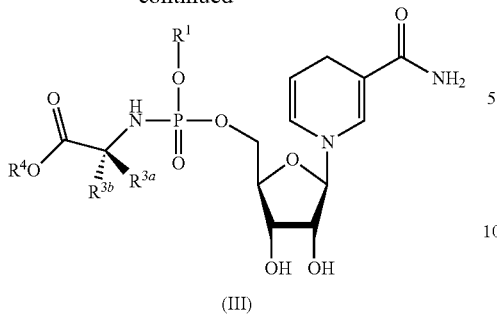

(III)

Compound 4 may be reacted with sodium dithionite to yield the triacetate 14. This compound (14) may then be reacted with a base such as sodium methoxide in MeOH to yield compound 15, followed by coupling of one of the hydroxyl groups of the nucleoside under basic conditions with the product of Scheme 1, compound 7 to produce the compound according to Formula (III).

EXEMPLIFICATION

Synthetic Preparation of Compound Embodiments

Abbreviations

Boc tert-butyloxycarbonyl
Ac acetyl
Ph phenyl
Tf trifluoromethanesulfonyl
DIPEA diisopropylethylamine
DCM dichloromethane
TFA trifluoroacetic acid
THF tetrahydrofuran
TMS trimethyl silane
TMSOTf trimethylsilyl trifluoromethanesulfonate
aq aqueous
M concencetration expressed in mol/L
rt room temperature
TLC thin lay chromatography
HPLC high-performance liquid chromatography
NMI 1-methyl imidazole
LCMS liquid chromatography-mass spectrometry
ESI+ m/z values in mass spectroscopy (Ionization ESI)
ESI− m/z values in mass spectroscopy (Ionization ESI)
$^1$H NMR (DMSO-$d_6$) δ (ppm) of peak in $^1$H NMR in DMSO-$d_6$
s singlet (spectrum)
d doublet (spectrum)
t triplet (spectrum)
q quartet (spectrum)
dd double doublet (spectrum)
br broad line (spectrum)
m multiplet (spectrum).

30

Example 1—Synthesis of 3-carbamoyl-1-((2R,3R,4S,5R)-3,4-dihydroxy-5-((((((S)-1-isopropoxy-1-oxopropan-2-yl)amino)(phenoxy)phosphoryl)oxy)methyl)-tetrahydrofuran-2-yl)pyridin-1-ium trifluoromethanesulfonate (Compound 1)

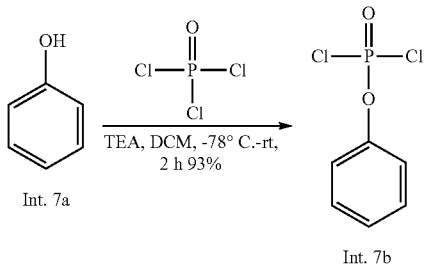 [SMILES: Oc1ccccc1 ; O=P(Cl)(Cl)Cl ; O=P(Cl)(Cl)Oc1ccccc1]

To a solution of POCl$_3$ (3.66 g, 23.8 mmol, 1.0 eq) in DCM (20 mL) was added dropwise a mixture of Intermediate 7a (2.0 g, 21.3 mmol, 1.0 eq) and TEA (2.15 g, 21.3 mmol, 1.0 eq) in DCM (10 mL) at −78° C. The mixture was warmed to room temperature and stirred for 2 h. The solvent was removed under reduced pressure. Ether (50 mL) was added and the mixture was filtered and the filter cake was washed with ether. The ether solution was dried over Na$_2$SO$_4$ and concentrated under reduced pressure to give Intermediate 7b (4.2 g, 93%) as a colorless oil. It was used for next step without further purification.

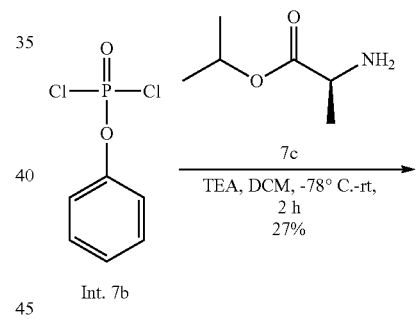

To a solution of compound Intermediate 7b (644 mg, 3.05 mmol, 1.0 eq) in DCM (15 mL) was added dropwise a mixture of Intermediate 7c (400 mg, 3.05 mmol, 1.0 eq) and TEA (308 mg, 3.05 mmol, 1.0 eq) in DCM (5 mL) at −78° C. The mixture was warmed to room temperature and stirred for 2 h. The solvent was removed under reduced pressure and ether (20 mL) was added. The mixture was filtered and the filter cake was washed with ether. The combined ether solution was dried over Na$_2$SO$_4$ and the solvent was removed. The residue was purified by flash chromatography on silica (petroleum ether/ethyl acetate=2:1) to give Intermediate 7 (257 mg, 27%) as a colorless oil.
LC-MS: 306 (M+1)$^+$ ¹H NMR (400 MHz, CDCl₃): δ 7.39-7.35 (m, 2H), 7.27-7.21 (m, 3H), 5.10-5.05 (m, 1H), 4.40-4.25 (m, 1H), 4.12-4.03 (m, 1H), 1.50-1.48 (m, 3H), 1.29-1.22 (m, 6H).

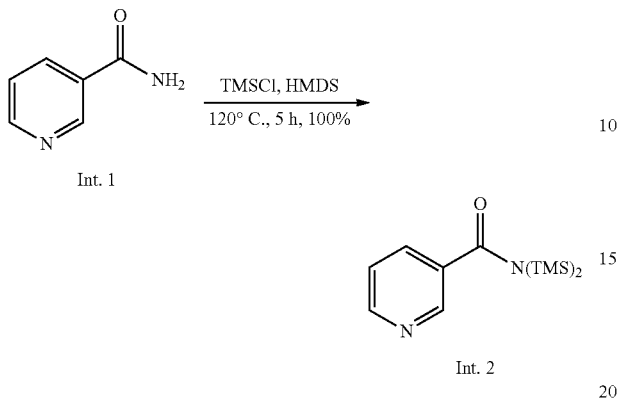

A suspension of Intermediate 1 (2.0 g, 17.86 mmol, 1.0 eq) and TMSCl (3.88 g, 35.72 mmol, 2.0 eq) in hexamethyldisilazane (HMDS) (30 mL) was stirred at 150° C. for 12 h. The clear solution was concentrated under reduced pressure to give Intermediate 2 (4.8 g, 100%) as a white solid.

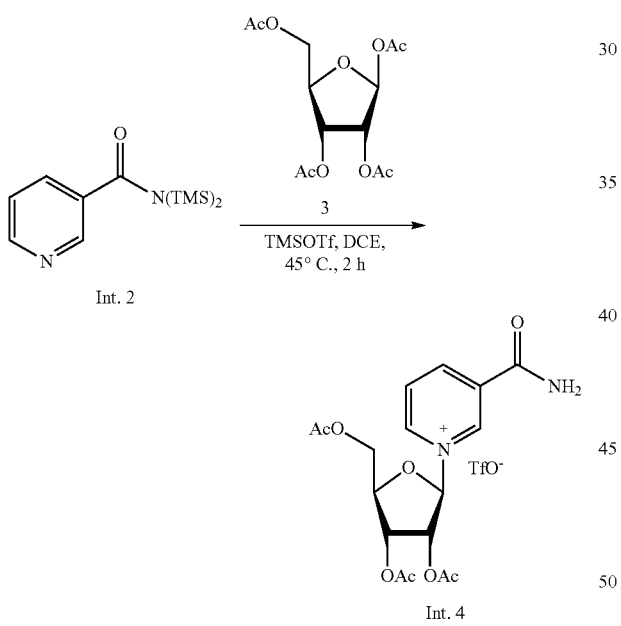

A mixture of Intermediate 2 (3.1 g, 17.86 mmol, 1.5 eq), Intermediate 3 (3.79 g, 11.9 mmol, 1.0 eq) and TMSOTf (13.2 g, 59.5 mmol, 5.0 eq) in DCE (50 mL) was stirred under N₂ at 45° C. for 2 h. The mixture was concentrated to give the crude product. Part of the crude product was purified by HPLC to give Intermediate 4 (144 mg) as a colorless oil.

LC-MS: 381 (M)⁺

¹H NMR (400 MHz, DMSO): δ 9.44 (s, 1H), 9.23 (d, J=6.8 Hz, 1H), 9.05 (d, J=8.4 Hz, 1H), 8.68 (s, 1H), 8.39-8.35 (m, 1H), 8.22 (s, 1H), 6.63 (d, J=2.8 Hz, 1H), 5.62-5.59 (m, 1H), 5.44-5.40 (m, 1H), 4.70-4.68 (m, 1H), 4.43 (s, 2H), 2.12-2.04 (m, 9H).

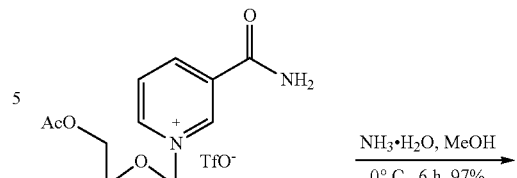

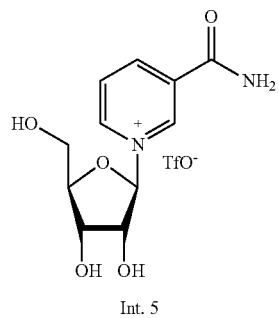

To a solution of Intermediate 4 (300 mg, 0.79 mmol, 1.0 eq) in MeOH (10 mL) was added NH₃—H₂O (2 mL) at 0° C. under nitrogen atmosphere. The mixture was stirred at 0° C. for 6 h. The mixture was concentrated under reduced pressure and the residue was purified by HPLC to give Intermediate 5 (223 mg, 97%) as a colorless oil.

LC-MS: 255 (M)⁺

¹H NMR (400 MHz, DMSO): δ 9.51 (s, 1H), 9.32 (d, J=6.0 Hz, 1H), 8.97 (d, J=7.6 Hz, 1H), 8.55 (s, 1H), 8.34-8.30 (m, 1H), 8.16 (s, 1H), 6.15 (d, J=4.4 Hz, 1H), 4.28-4.22 (m, 2H), 4.11 (t, J=4.4 Hz, 1H), 3.83-3.78 (m, 1H), 3.71-3.66 (m, 1H).

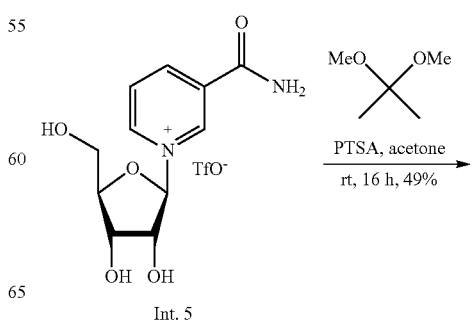

-continued

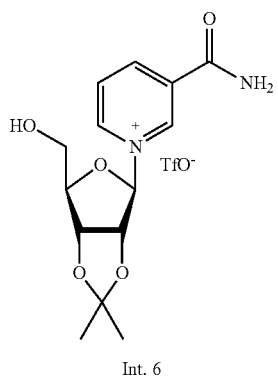

Int. 6

A mixture of Intermediate 5 (230 mg, 0.9 mmol, 1.0 eq), acetone dimethyl acetal (938 mg, 9.0 mmol, 10.0 eq), PTSA (31 mg, 0.18 mmol, 0.2 eq) in acetone (5 mL) was stirred at room temperature for 16 h. The reaction was monitored by TLC. The resulting mixture was filtered and the filtrate was concentrated under reduced pressure. The residue was purified by prep-TLC (DCM/MeOH=4:1) to give Intermediate 6 (125 mg, 49%) as a slightly yellow oil.

LC-MS: 295 (M)+

$^1$H NMR (400 MHz, DMSO): δ 9.42 (s, 1H), 9.28 (d, J=6.0 Hz, 1H), 9.01-8.99 (m, 1H), 8.72 (br, s, 1H), 8.28-8.24 (m, 1H), 8.15 (br s, 1H), 6.45 (s, 1H), 5.33 (t, J=4.4 Hz, 1H), 5.24-5.22 (m, 1H), 4.91 (d, J=6.0 Hz, 1H), 4.69 (s, 1H), 3.75-3.62 (m, 2H), 1.56 (s, 3H), 1.33 (s, 3H).

To a solution of Intermediate 6 (50 mg, 0.17 mmol, 1.0 eq) and N-methylimidazole (111 mg, 1.3 mmol, 8.0 eq) in THF (2 mL) under N$_2$ was added Intermediate 7 (337 mg, 1.1 mmol, 6.5 eq) in THF (1 mL). The mixture was monitored by LC-MS and stirred at room temperature for 3 h. A second portion of N-methylimidazole (111 mg, 1.3 mmol, 8.0 eq) and 7 (337 mg, 1.1 mmol, 6.5 eq) in THF (1 mL) was added to the reaction mixture. The resulting mixture was stirred at room temperature for another 3 h, and then filtered. The filtrate was concentrated under reduced pressure and the residue was purified by preparative-TLC (PE/EA=3:1) to give Intermediate 8 (25 mg, 31%) as a yellow oil.

LC-MS: 564 (M)+

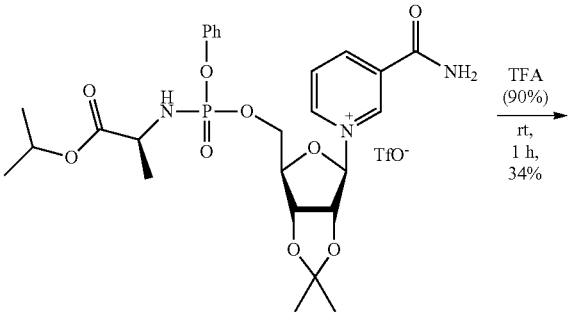

Int. 8

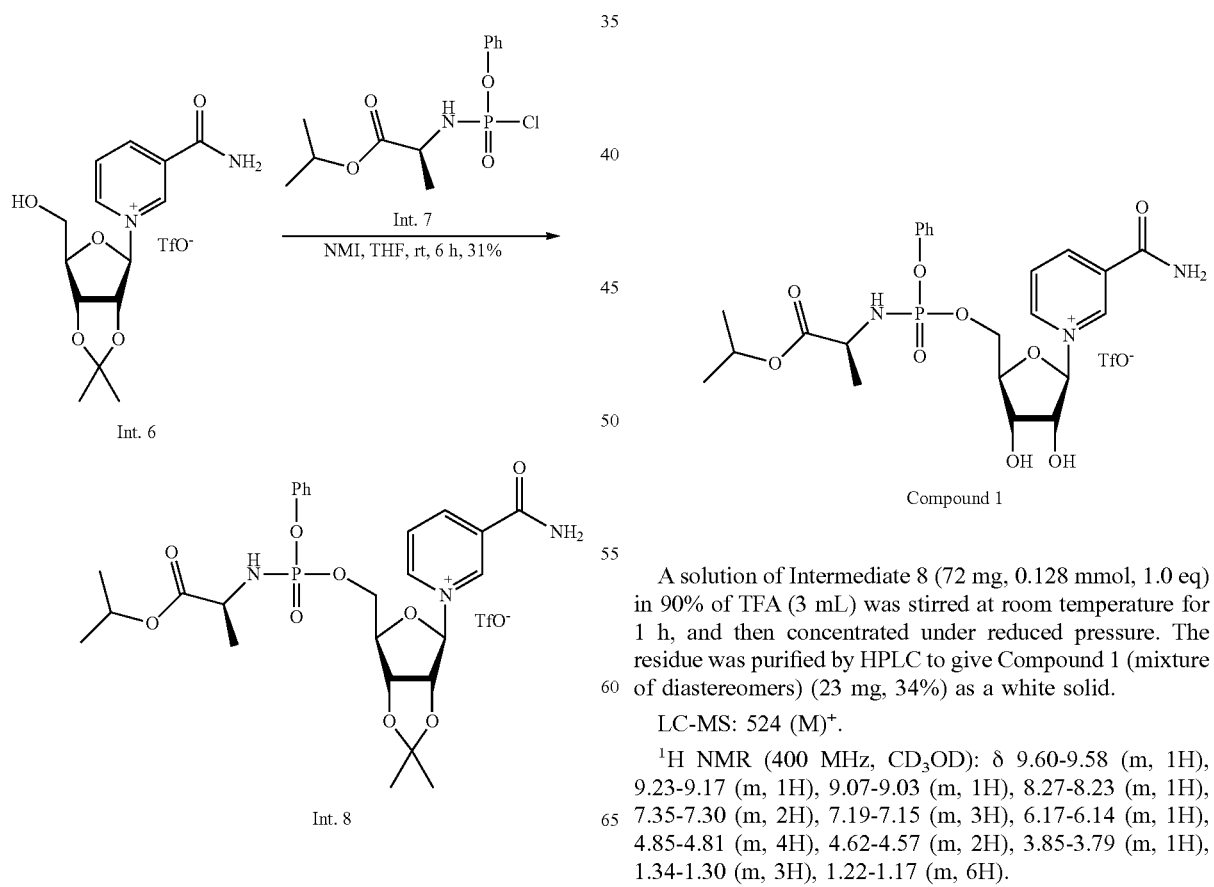

A solution of Intermediate 8 (72 mg, 0.128 mmol, 1.0 eq) in 90% of TFA (3 mL) was stirred at room temperature for 1 h, and then concentrated under reduced pressure. The residue was purified by HPLC to give Compound 1 (mixture of diastereomers) (23 mg, 34%) as a white solid.

LC-MS: 524 (M)+.

$^1$H NMR (400 MHz, CD$_3$OD): δ 9.60-9.58 (m, 1H), 9.23-9.17 (m, 1H), 9.07-9.03 (m, 1H), 8.27-8.23 (m, 1H), 7.35-7.30 (m, 2H), 7.19-7.15 (m, 3H), 6.17-6.14 (m, 1H), 4.85-4.81 (m, 4H), 4.62-4.57 (m, 2H), 3.85-3.79 (m, 1H), 1.34-1.30 (m, 3H), 1.22-1.17 (m, 6H).

Example 2: 3-Carbamoyl-1-((2R,3R,4S,5R)-3,4-dihydroxy-5-((((((S)-1-methoxy-1-oxopropan-2-yl)amino)(phenoxy)phosphoryl)oxy)methyl)tetrahydrofuran-2-yl)pyridin-1-ium trifluoromethanesulfonate (Compound 2)

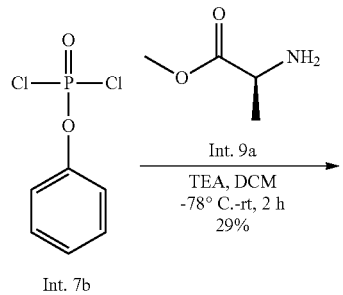

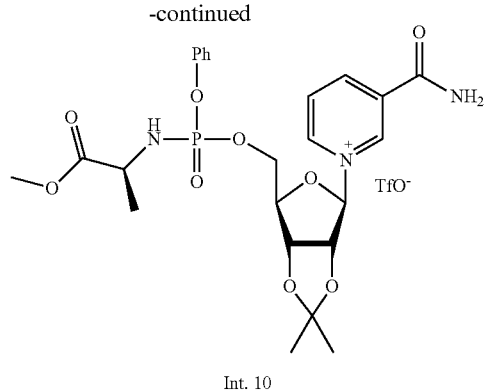

To a solution of Intermediate 7a (10.0 g, 47.4 mmol, 1.0 eq) in DCM (100 mL) at −78° C. under nitrogen atmosphere was added dropwise a mixture of Intermediate 9a (4.88 g, 47.4 mmol, 1.0 eq) and TEA (4.79 g, 47.4 mmol, 1.0 eq) in DCM (40 mL). The mixture was warmed to rt and stirred for 2 h. The reaction was monitored by TLC. The solvent was removed under reduced pressure and ether (120 mL) was added. The mixture was filtered and the filter cake was washed with ether. The residue was concentrated under reduced pressure and purified by flash chromatography on silica gel (PE/EA=20:1~4:1) to give Intermediate 9 (3.86 g, 29%) as a colorless oil.

LC-MS: 278 (M)$^+$

To a solution of Intermediate 6 (300 mg, 1.02 mmol, 1.0 eq) and NMI (667 mg, 8.1 mmol, 8.0 eq) in THF (8 mL) under N$_2$ was added Intermediate 9 (1.8 g, 6.6 mmol, 6.5 eq) in THF (8 mL). The mixture was stirred at rt for 3 h. The reaction was monitored by TLC. The THF phase was isolated and the solvent was removed. The residue was purified by preparative TLC (DCM/MeOH=7:1) to give Intermediate 10 (434 mg, 94%) as a colorless oil.

LC-MS: 536 (M$^+$)

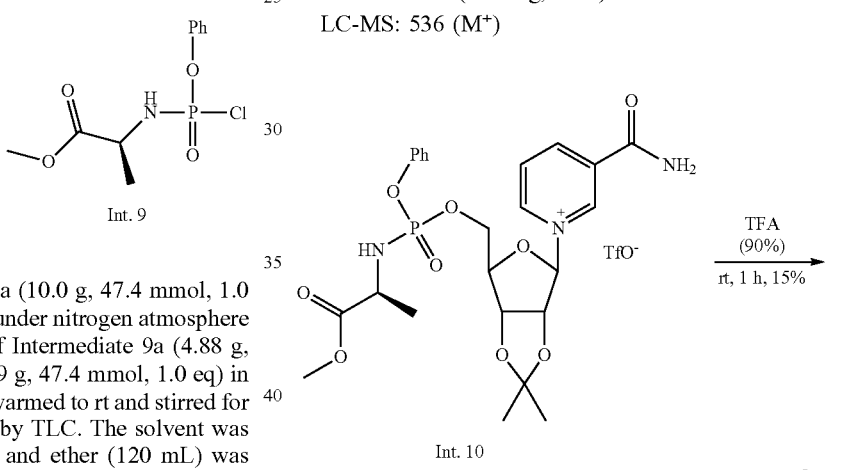

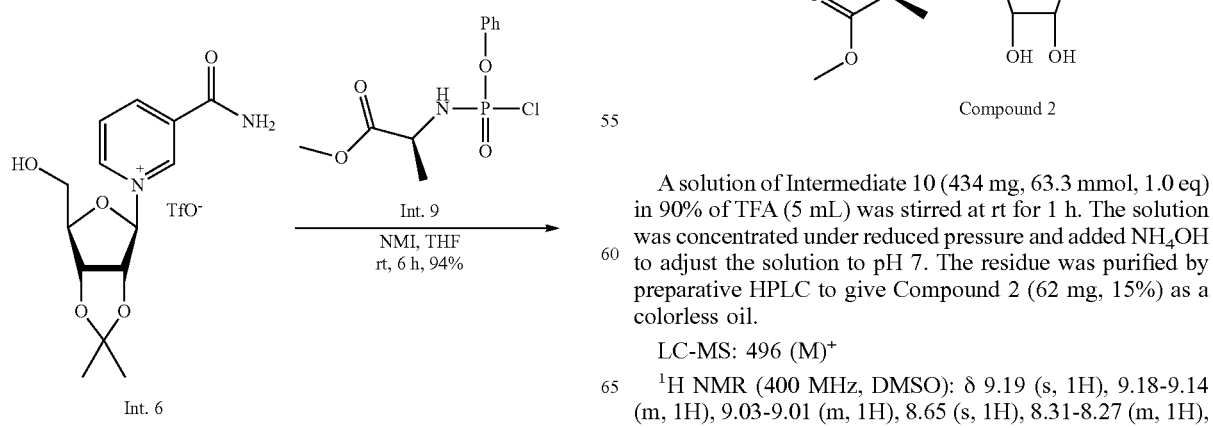

A solution of Intermediate 10 (434 mg, 63.3 mmol, 1.0 eq) in 90% of TFA (5 mL) was stirred at rt for 1 h. The solution was concentrated under reduced pressure and added NH$_4$OH to adjust the solution to pH 7. The residue was purified by preparative HPLC to give Compound 2 (62 mg, 15%) as a colorless oil.

LC-MS: 496 (M)$^+$ $^1$H NMR (400 MHz, DMSO): δ 9.19 (s, 1H), 9.18-9.14 (m, 1H), 9.03-9.01 (m, 1H), 8.65 (s, 1H), 8.31-8.27 (m, 1H), 8.21 (s, 1H), 7.36-7.31 (m, 2H), 7.20-7.13 (m, 3H), 6.19-

6.07 (m, 2H), 4.45-4.34 (m, 3H), 4.22-4.18 (m, 1H), 4.12-4.09 (m, 1H), 3.88-3.85 (m, 1H), 3.55-3.53 (m, 3H), 1.21-1.18 (m, 3H).

Example 3: 3-Carbamoyl-1-((2R,3R,4S,5R)-5-((((((S)-1-(cyclohexyloxy)-1-oxopropan-2-yl)amino)(phenoxy)phosphoryl)oxy)methyl)-3,4-dihydroxytetrahydrofuran-2-yl)pyridin-1-ium trifluoromethanesulfonate (Compound 3)

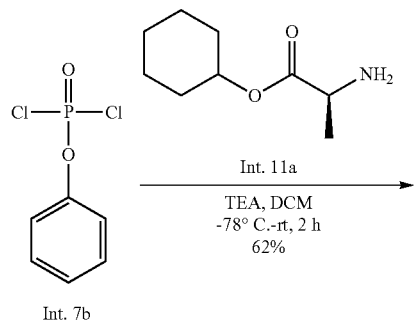

Int. 7b

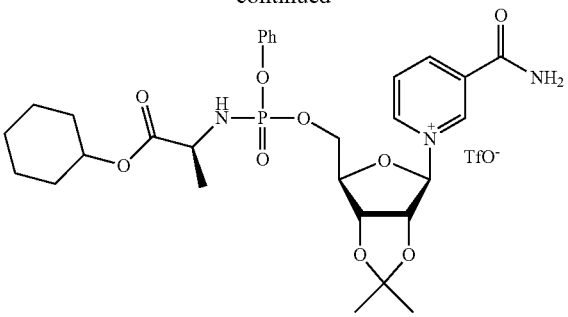

Int. 12

To a solution of Intermediate 6 (448 mg, 1.52 mmol, 1.0 eq) and NMI (996 mg, 12.1 mmol, 8.0 eq) in THF (8 mL) under N₂ was added a solution of Intermediate 11 (3.4 g, 9.87 mmol, 6.5 eq) in THF (8 mL). The mixture was stirred at rt for 3 h. The reaction was monitored by TLC. The resulting mixture was filtered and the filtrate was concentrated under reduced pressure and purified by flash chromatography on silica (DCM/MeOH=20:1) to give compound 7 (1.67 g, 100%) as a yellow solid.

LC-MS: 604 (M⁺)

Int. 11

To a solution of Intermediate 7b (10.0 g, 47.4 mmol, 1.0 eq) in DCM (100 mL) at −78° C. under nitrogen atmosphere was added dropwise a mixture of Intermediate 11a (8.1 g, 47.4 mmol, 1.0 eq) and TEA (4.79 g, 47.4 mmol, 1.0 eq) in DCM (40 mL). The mixture was warmed to rt and stirred for 2 h. The reaction was monitored by TLC. The solvent was removed under reduced pressure and ether (120 mL) was added. The mixture was filtered and the filter cake was washed with ether. The residue was concentrated under reduced pressure and purified by flash chromatography on silica (PE/EA=10:1) to give Intermediate 11 (10.2 g, 62%) as a yellow oil. LC-MS: 346 (M)⁺

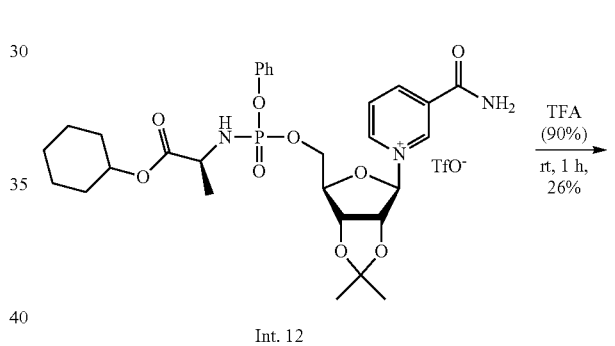

Int. 12

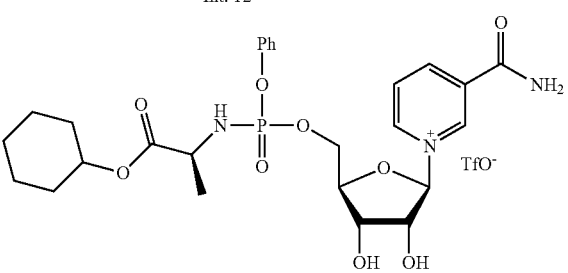

Compound 3

A solution of Intermediate 12 (1.62 g, 2.2 mmol, 1.0 eq) in 90% of TFA (5 mL) was stirred at rt for 1 h. Then the solution was concentrated under reduced pressure. The residue was purified by preparative HPLC to give Compound 3 (188 mg, 26%) as a colorless oil.

LC-MS: 564 (M)⁺

¹H NMR (400 MHz, DMSO-d6): δ 9.39 (s, 1H), 9.20-9.14 (m, 1H), 9.03-8.99 (m, 1H), 8.65 (s, 1H), 8.31-8.24 (m, 1H), 8.21 (s, 1H), 7.36-7.29 (m, 2H), 7.19-7.13 (m, 3H), 6.19-6.17 (m, 1H), 6.16-6.10 (m, 1H), 4.56-4.55 (m, 1H), 4.44-4.09 (m, 4H), 3.96-3.77 (m, 2H), 1.61-1.58 (m, 4H), 1.31-1.28 (m, 1H), 1.26-1.23 (m, 5H), 1.22-1.18 (m, 3H).

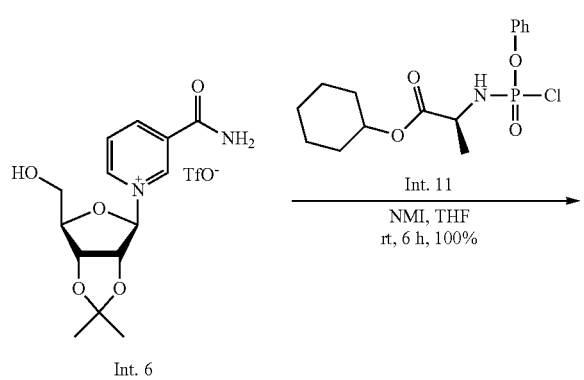

Int. 6

Example 4: Methyl ((((2R,3S,4R,5R)-5-(3-carbamoylpyridin-1(4H)-yl)-3,4-dihydroxytetrahydrofuran-2-yl)methoxy)(phenoxy)phosphoryl)-L-alaninate (Compound 4)

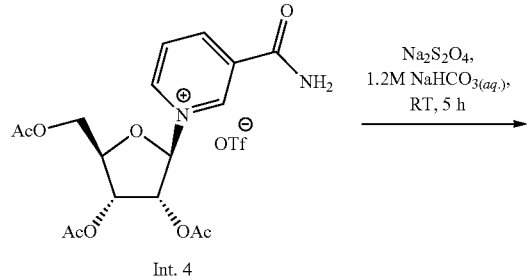

Int. 4

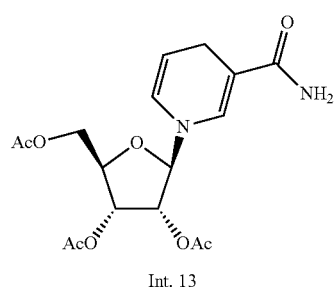

Int. 13

To a stirred solution of Int. 4 (2.5 g, 4.71 mmol) in degassed 1.2 M NaHCO$_{3(aq.)}$ (18 mL) was added sodium dithionite (1.64 g, 9.43 mmol) in small portions at room temperature. The resulting mixture was stirred for 5 h, then extracted with DCM (4×50 mL). The combined organic layers were washed with brine (50 mL), dried over anhydrous Na$_2$SO$_4$ and concentrated under reduced pressure. The crude residue was purified by flash chromatography (60 g of 100-200 silica gel, 3% MeOH-DCM) to afford Int. 13 (0.36 g, 20% yield) as a pale yellow foamy solid.

LC-MS: m/z: 383.57 [M+1]$^+$ $^1$H NMR (400 MHz, CD$_3$OD): δ 7.16 (d, J=0.8 Hz, 1H), 6.06 (dd, J=1.6, 8.4 Hz, 1H), 5.27-5.20 (m, 2H), 5.04 (d, J=7.2 Hz, 1H), 4.90-4.85 (m, 1H), 4.28-4.26 (m, 2H), 4.24-4.20 (m, 1H), 3.07 (dd, J=1.6, 3.2 Hz, 2H), 2.14 (s, 3H), 2.10 (s, 3H), 2.07 (s, 3H).

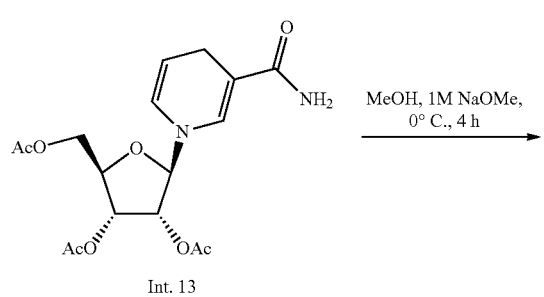

Int. 13

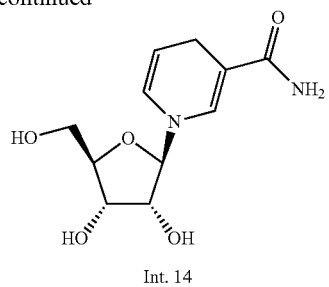

Int. 14

To a stirred solution of Int. 13 (2.7 g, 7.06 mmol) in MeOH (56 mL) was added NaOCH$_3$ (7.0 mL, 7.0 mmol, 1M in MeOH) dropwise at 0° C. under Ar. The reaction mixture was stirred at 0° C. for 4 h. After completion of the reaction (monitored by TLC), the reaction mixture was concentrated under reduced pressure (water bath, temperature of the rotovap was ~30° C.) and the residue was quickly purified by flash chromatography (80 g of 100-200 silica gel, 30% MeOH-DCM) to afford Int. 14 (1.4 g, 77% yield) as a yellow foamy solid.

LC-MS: m/z: 257.59 [M+1]$^+$ $^1$H NMR (400 MHz, DMSO-d$_6$): δ 6.94 (s, 1H), 6.64 (brs, 2H, -2NH), 6.09 (d, J=8.0, 1H), 5.17 (brs, 1H, —OH), 5.01 (brs, 1H, —OH), 4.86 (brs, 1H, —OH), 4.67 (dt, J=3.2, 8.0 Hz, 1H), 4.59 (d, J=6.8 Hz 1H), 3.88-3.81 (m, 2H), 3.71-3.65 (m, 1H), 3.46-3.43 (m, 2H), 3.16 (s, 1H), 2.94 (s, 2H).

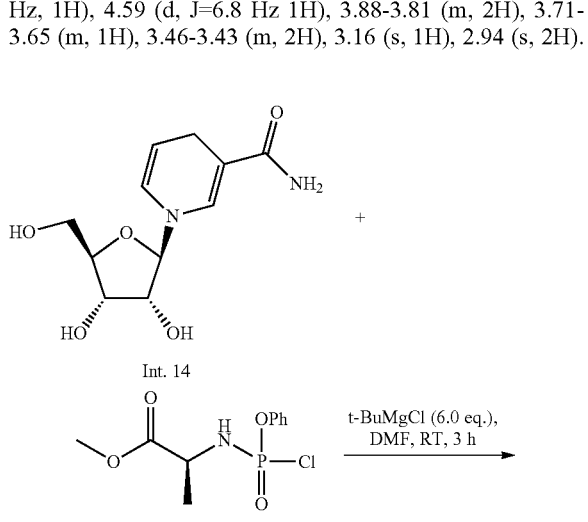

Int. 9

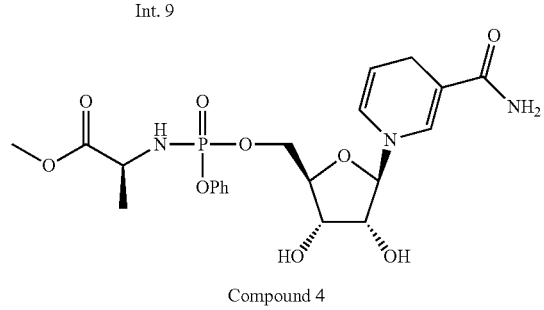

Compound 4

To a stirred solution of Int. 14 (1.0 g, 3.90 mmol) in dry DMF (20 mL) was added t-BuMgCl (23.4 mL, 23.4 mmol, 1M in 2-MeTHF) dropwise over a period of 15 minutes at room temperature under Ar atmosphere. The resulting white suspension was stirred for 15 minutes, then added a solution of Int. 9 (6.5 g, 23.4 mmol) in dry DMF (7 mL) dropwise.

The resulting clear pale yellow solution was stirred at room temperature for 3 h. The reaction mixture was quenched with MeOH (2 mL) at room temperature and the resulting mixture was concentrated under reduced pressure. The crude residue was purified by flash chromatography (150 g of 100-200 silica gel, 10% MeOH-DCM) to afford Compound 4 (200 mg, 38.7% LCMS) which was further purified by Prep-HPLC to give pure Compound 4 (23 mg, 1.18% yield) as a mixture of two diastereomers (hygroscopic white fluffy solid).

LC-MS: m/z: 498.72 [M+1]$^+$ $^1$H NMR (400 MHz, DMSO-d$_6$): δ 7.39-7.35 (m, 2H), 7.21-7.15 (m, 3H), 6.99 (s, 1H), 6.69 (brs, 2H, -2NH), 6.11-5.99 (m, 2H, -1NH), 5.24 (brs, 1H, —OH), 5.15 (brs, 1H, —OH), 4.69-4.63 (m, 2H), 4.12-3.97 (m, 3H), 3.86-3.80 (m, 3H), 3.59 (s, 3H), 2.94 (s, 2H), 1.22 (dd, J=6.8, 10.8 Hz, 3H).

Example 5: (2S)-Cyclohexyl2-(((((2R,3S,4R,5R)-5-(3-carbamoylpyridin-1(4H)-yl)-3,4-dihydro-xytetra-hydrofuranyl)methoxy)(phenoxy)phosphoryl)amino) propanoate, (Compound 5)

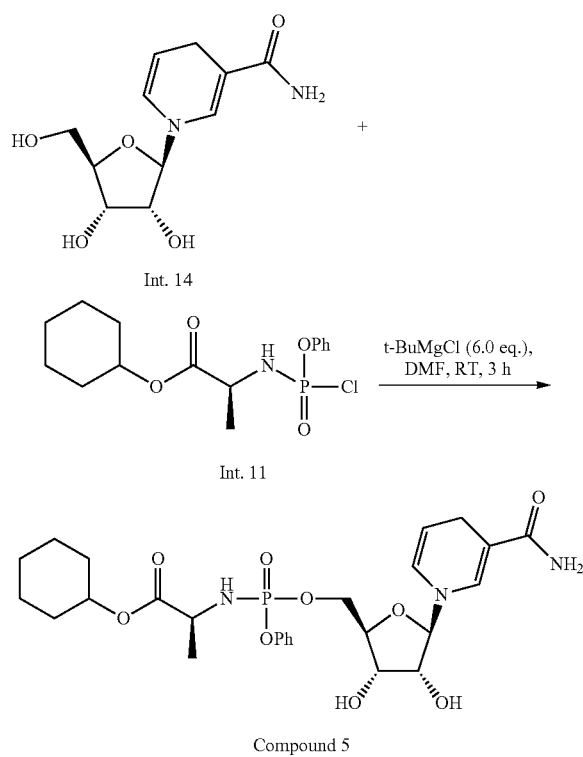

MeOH-DCM) to afford Compound 5 (510 mg, 25.7% LCMS) which was further purified by Prep-HPLC to give Compound 5 (18 mg, 0.98%) as a mixture of two diastereomers (hygroscopic white fluffy solid).

LC-MS: m/z: 566.82 [M+1]$^+$ $^1$H NMR (400 MHz, DMSO-d$_6$): δ 7.38-7.32 (m, 2H), 7.22-7.15 (m, 3H), 6.98 (s, 1H), 6.68 (brs, 2H, -2NH), 6.05-5.96 (m, 2H, -1NH), 5.27 (brs, 1H, —OH), 5.19 (brs, 1H, —OH), 4.66-4.62 (m, 3H), 4.10-3.99 (m, 2H), 3.87-3.77 (m, 4H), 2.94 (s, 2H), 1.77-1.64 (m, 5H), 1.44-1.18 (m, 8H).

Example 6: (2S)-Isopropyl-2-(((((2R,3S,4R,5R)-5-(3-carbamoylpyridin-1(4H)-yl)-3,4-dihydroxy-tetra-hydrofuranyl)methoxy)(phenoxy)phosphoryl)amino) propanoate, (Compound 6)

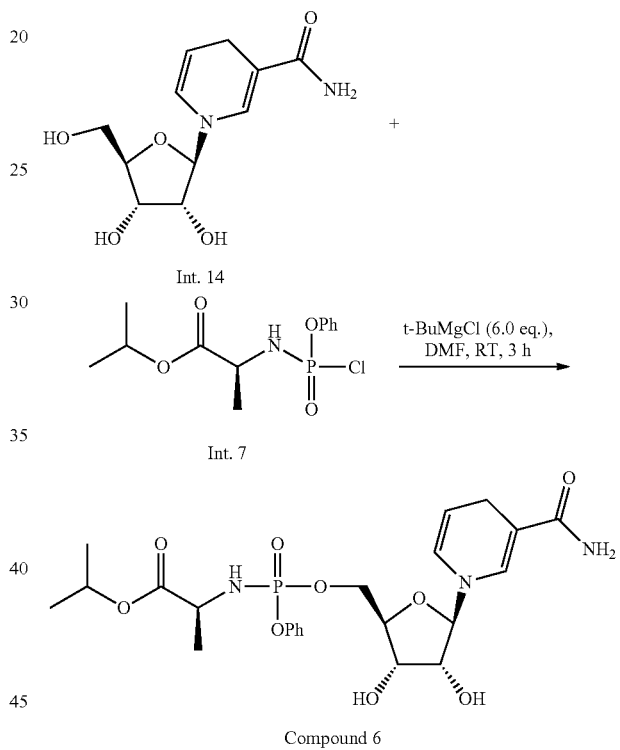

To a stirred solution of Int. 14 (1.0 g, 3.90 mmol) in dry DMF (20 mL) was added t-BuMgCl (23.4 mL, 23.4 mmol, 1M in 2-MeTHF) dropwise over a period of 15 minutes at room temperature under Ar atmosphere. The resulting white suspension was stirred for 15 minutes, then added a solution of Int. 7 (7.15 g, 23.4 mmol) in dry DMF (7 mL) dropwise. The resulting clear pale yellow solution was stirred at room temperature for 3 h. The reaction mixture was quenched with MeOH (2 mL) and concentrated under reduced pressure. The crude residue was purified by flash chromatography (150 g of 100-200 silica gel, 7% MeOH-DCM) to afford Compound 6 (510 mg, 25.5% LCMS), which was further purified by Prep-HPLC to give Compound 6 (20 mg, 0.98%) as a mixture of two diastereomers (hygroscopic white fluffy solid).

LC-MS: m/z: 526.80 [M+1]$^+$ $^1$H NMR (400 MHz, DMSO-d$_6$): δ 7.38-7.29 (m, 2H), 7.22-7.15 (m, 3H), 6.98 (s, 1H), 6.68 (brs, 2H, -2NH), 6.05-5.99 (m, 2H, -1NH), 5.22 (brs, 1H, —OH), 5.14 (brs, To a stirred solution of Int. 14 (1.0 g, 3.90 mmol) in dry DMF (20 mL) was added t-BuMgCl (23.4 mL, 23.4 mmol, 1M in 2-MeTHF) dropwise over a period of 15 minutes at room temperature under Ar atmosphere. The resulting white suspension was stirred for 15 minutes, then added a solution of Int. 11 (8.10 g, 23.4 mmol) in dry DMF (8 mL) dropwise under Ar atmosphere. The resulting clear pale yellow solution was stirred at room temperature for 3 h. The reaction mixture was quenched with MeOH (2 mL) at room temperature and the resulting mixture was concentrated under reduced pressure. The crude residue was purified by flash column chromatography (160 g of 100-200 silica gel, 5%

1H, —OH), 4.88-4.83 (m, 1H), 4.67-4.62 (m, 2H), 4.09-3.88 (m, 2H), 3.85-3.75 (m, 4H), 2.95 (s, 2H), 1.23-1.11 (m, 9H).

Example 7: 3-Carbamoyl-1-((2R,3R,4S,5R)-3,4-dihydroxy-5-((((((S)-1-methoxy-1-oxopropan-2-yl)amino)(phenoxy)phosphoryl)oxy)methyl)tetrahydrofuran-2-yl)pyridin-1-ium chloride (Compound 7)

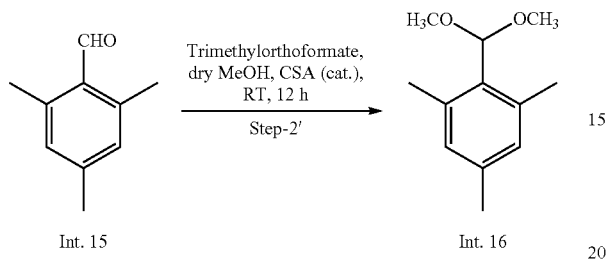

To a stirred solution of Int. 15 (10 g, 67.47 mmol) in dry MeOH (80 mL), trimethyl orthoformate (11.2 mL, 101.2 mmol) and CSA (15 mg) were added at room temperature under Ar atmosphere. The reaction mixture was stirred 12 h, then poured into saturated aqueous NaHCO₃ solution (100 mL) and stirred for 10 minutes. The resulting mixture was extracted with diethyl ether (2×50 mL), and the combined extracts were washed with brine (50 mL). The organic layer was dried over Na₂SO₄ and concentrated under reduced pressure. The residue was again diluted with diethyl ether (25 mL) and dried over Na₂SO₄. The solution was filtered and the filtrate was concentrated in vacuo to afford Int. 16 (12 g, 92% yield) as a colorless oil.

$R_f$=0.6 (Mobile phase: 2% EtOAc-hexanes).

¹H NMR (400 MHz, CDCl₃): δ 6.82 (s, 2H), 5.48 (s, 1H), 3.41 (s, 6H), 2.42 (s, 6H), 2.26 (s, 3H).

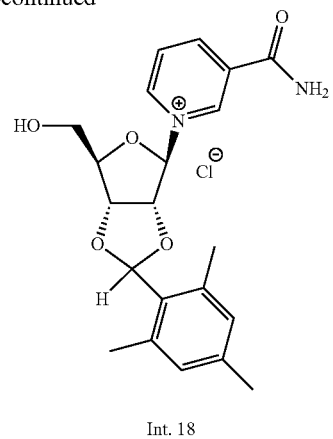

To a stirred suspension of Int. 17 (1 g, 3.92 mmol) in dry DMF (40 mL), mesitaldehyde dimethyl acetal (Int. 16) (2.28 g, 11.75 mmol) was added followed by cat. CSA (10 mg) at room temperature. After 30 minutes the reaction mixture became a clear solution and after 1 h white precipitation was observed. The resulting mixture was stirred at room temperature for 4 h, the reaction mixture was filtered and the precipitate was washed with diethyl ether (2×10 mL) and dried under vacuum to afford Int. 18 (400 mg, 26.6% yield) as a white solid.

LC-MS: m/z: 385.79 [M]⁺

¹H NMR (400 MHz, DMSO-d₆): δ 9.46 (s, 1H), 9.34 (d, J=6.0 Hz, 1H), 9.08 (d, J=8.0, 1H), 8.89 (brs, 1H, —NH), 8.27 (t, J=6.8 Hz 1H), 8.17 (brs, 1H, —NH), 6.89 (s, 2H), 6.69 (s, 1H), 6.21 (s, 1H), 5.43 (d, J=6.4 Hz, 2H), 5.0 (d, J=6.8 Hz, 1H), 4.96 (brs, 1H, —OH), 3.77-3.66 (m, 2H), 2.42 (s, 6H), 2.24 (s, 3H).

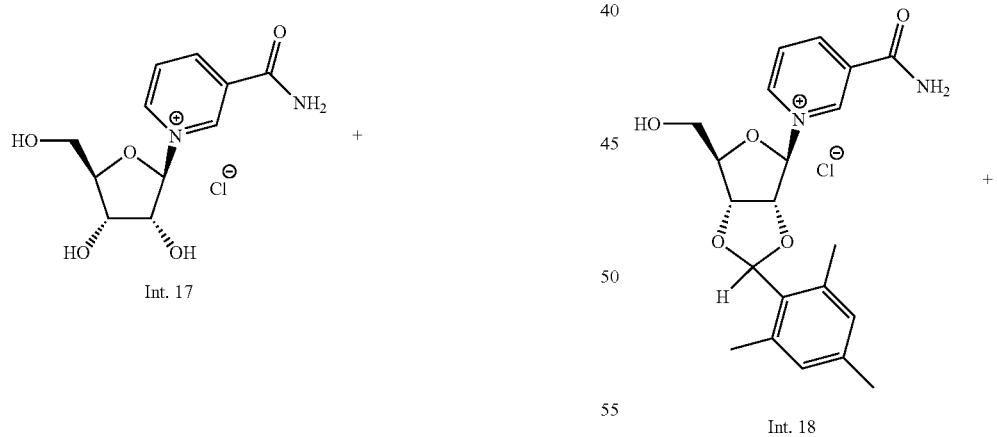

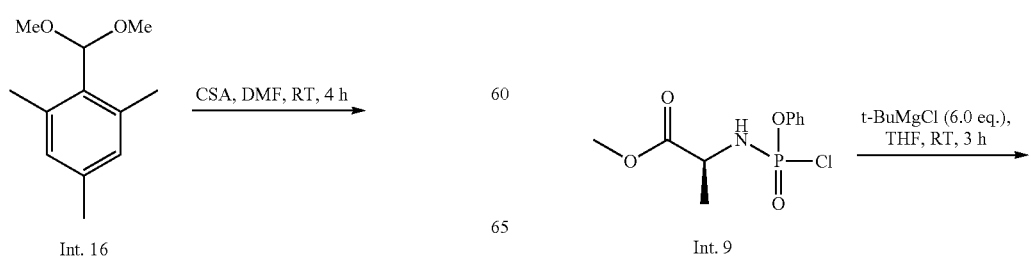

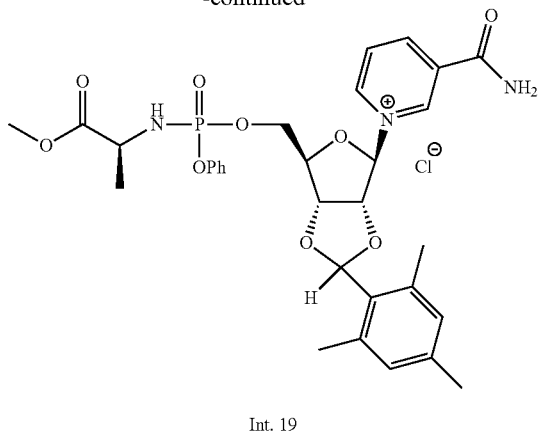

Int. 19

To a stirred suspension of Int. 18 (0.5 g, 1.29 mmol) in dry THF (20 mL) was added t-BuMgCl (7.8 mL, 7.8 mmol, 1.0 M in 2-MeTHF) dropwise over a period of 15 minutes at room temperature under Ar atmosphere. After 15 minutes, a solution of Int. 9 (1.08 g, 3.8 mmol) in dry THF (2 mL) was added dropwise. The resulting clear pale yellow solution was stirred at room temperature for 3 h, then the access base was quenched with methanol (2 mL). The resulting mixture was concentrated under reduced pressure. The crude residue was purified by flash column chromatography (300 g of 100-200 silica gel, 30% EtOAc-hexanes) to afford Int. 19 (0.8 g) as a pale yellow thick syrup, which was used in the next reaction without further purification.

LC-MS: m/z: 626.84 [M]+

$R_f$=0.3 (Mobile phase: 20% MeOH-DCM).

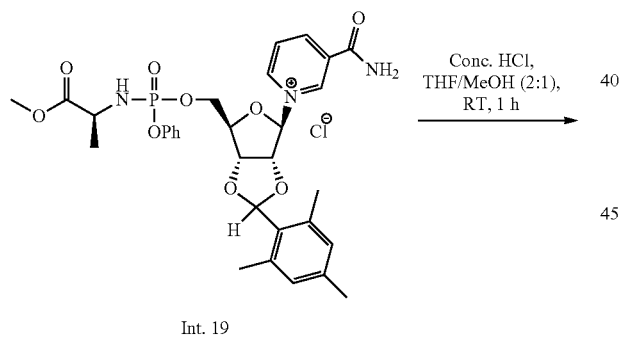

Int. 19

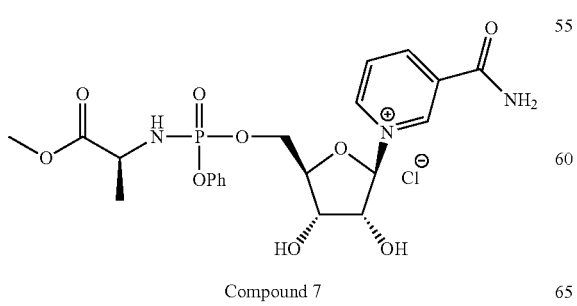

Compound 7

To a stirred solution of crude Int. 19 (1.6 g, 0.5 mmol) in a mixture of THF/MeOH (2:1, 45 mL) was added conc. HCl (0.5 mL) at room temperature. The resulting mixture was stirred for 1 h. The volatiles were removed under reduced pressure and the residue was purified column chromatography (200 g of 100-200 silica gel, 20% MeOH-DCM) to afford Compound 7 (100 mg, 88% LCMS), which was further purified by Prep-HPLC to afford Compound 7 (19 mg, 1.47% yield over two steps) as a hygroscopic white fluffy solid.

LC-MS: m/z: 496.73 [M]+

$^1$H NMR (400 MHz, DMSO-$d_6$): δ 9.39 (s, 1H), 9.17 (d, J=6.0 Hz, 1H), 9.01 (d, J=8.0 Hz, 1H), 8.65 (brs, 1H, —NH), 8.29 (t, J=6.8 Hz, 1H), 8.23 (brs, 1H, —NH), 7.37-7.33 (m, 2H), 7.20-7.15 (m, 3H), 6.19 (d, J=4.4 Hz, 1H), 6.14 (brs, 1H, —OH), 6.05 (brs, 1H, —OH), 5.74 (brs, 1H, —OH), 4.46-4.30 (m, 3H), 4.20-4.11 (m, 2H), 3.92-3.85 (m, 1H), 3.55 (s, 3H), 1.22 (d, J=7.2 Hz, 3H).

Example 8: 3-Carbamoyl-1-((2R,3R,4S,5R)-5-((((((S)-1-(cyclohexyloxy)-1-oxopropan-2-yl)-amino)(phenoxy)phosphoryl)oxy)methyl)-3,4-dihydroxytetrahydrofuran-2-yl)-pyridin-1-ium chloride, (Compound 8)

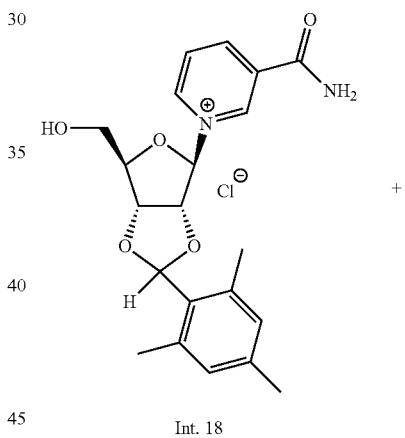

Int. 18

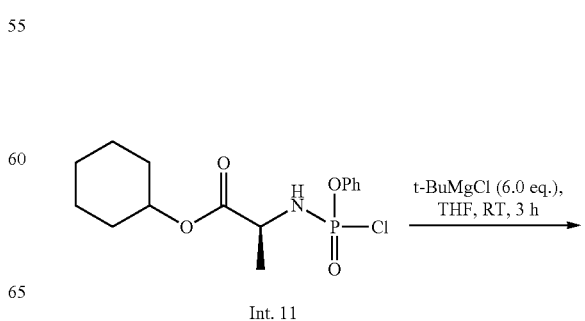

Int. 11

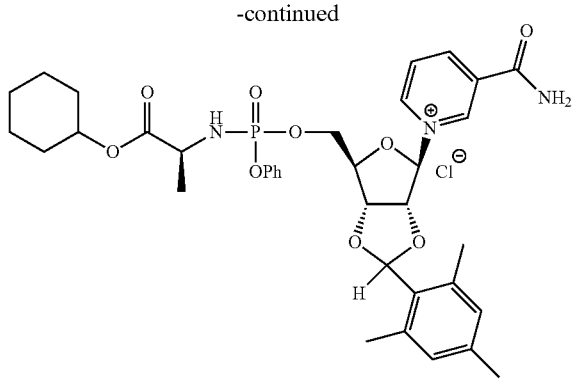

Int. 20

To a stirred suspension of Int. 18 (0.5 g, 1.29 mmol) in dry THF (20 mL) was added t-BuMgCl (7.8 mL, 7.8 mmol, 1.0 M in 2-MeTHF) dropwise over a period of 15 minutes at RT under Ar atmosphere. After stirring for 15 minutes, a solution of Int. 11 (1.34 g, 3.88 mmol) in dry THF (2 mL) was added dropwise. The resulting clear pale yellow solution was stirred for 3 h, then excess base was quenched with methanol (2 mL) at room temperature. The resulting mixture was concentrated under reduced pressure. The residue was purified by flash column chromatography (300 g of 100-200 silica gel, 20% MeOH-DCM) to afford Int. 20 (0.9 g) as a thick, pale yellow syrup, which was used in the next reaction without further purification.

LC-MS: m/z: 694.91 [M]$^+$ $R_f$=0.4 (Mobile phase: 20% MeOH-DCM).

To a stirred solution of Int. 20 (1.8 g, 0.57 mmol) in a mixture of THF/MeOH (2:1) (60 mL) was added 0.5N HCl (1.5 mL) at room temperature. The resulting mixture was stirred for 1 h, and volatiles were removed under reduced pressure. The residue was purified by column chromatography (100 g of 100-200 silica gel, 20% MeOH-DCM) to afford Compound 8 (250 mg, 73.4% LCMS), which was further purified by Prep-HPLC to afford Compound 8 (35 mg, 2.4% yield over two steps) as a hydroscopic, white fluffy solid.

LC-MS: m/z: 564.87 [M]$^+$ $^1$H NMR (400 MHz, DMSO-d$_6$): δ 9.40 (s, 1H), 9.27 (d, J=6.0 Hz, 1H), 9.02 (d, J=8.0 Hz, 1H), 8.66 (brs, 1H, —NH), 8.27 (t, J=6.4 Hz, 1H), 8.23 (brs, 1H, —NH), 7.35-7.31 (m, 2H), 7.20-7.16 (m, 3H), 6.20-6.05 (m, 3H, –2OH), 5.76 (brs, 1H), 4.61-4.59 (m, 1H), 4.42-4.28 (m, 3H), 4.20 (d, J=4.8 Hz, 1H), 4.11 (s, 1H), 3.88-3.81 (m, 1H), 1.69-1.61 (m, 4H), 1.45-1.24 (m, 6H), 1.22 (t, J=6.8 Hz, 3H).

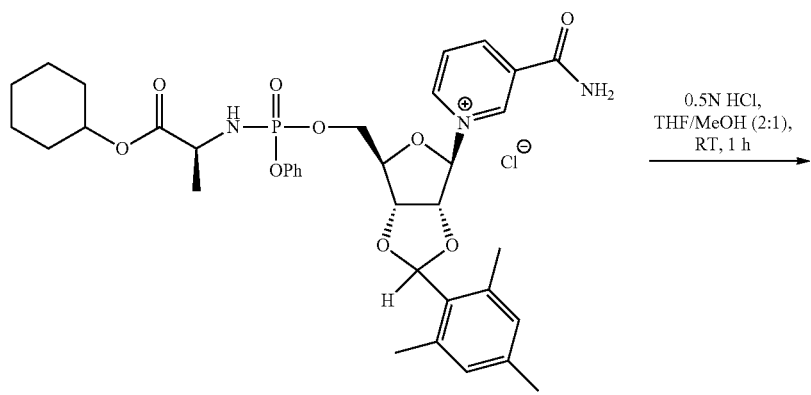

Int. 20

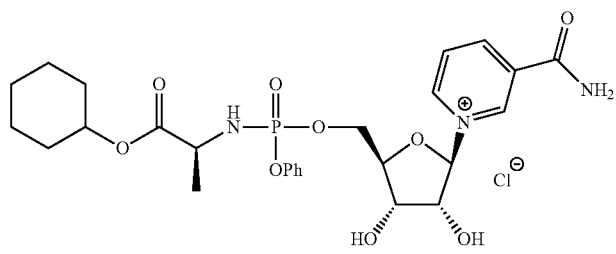

Compound 8

Example 9: 3-Carbamoyl-1-((2R,3R,4S,5R)-3,4-dihydroxy-5-((((((S)-1-isopropoxy-1-oxopropan-2-yl)amino)(phenoxy)phosphoryl)oxy)methyl)tetrahydrofuran-2-yl)pyridin-1-ium chloride (Compound 9)

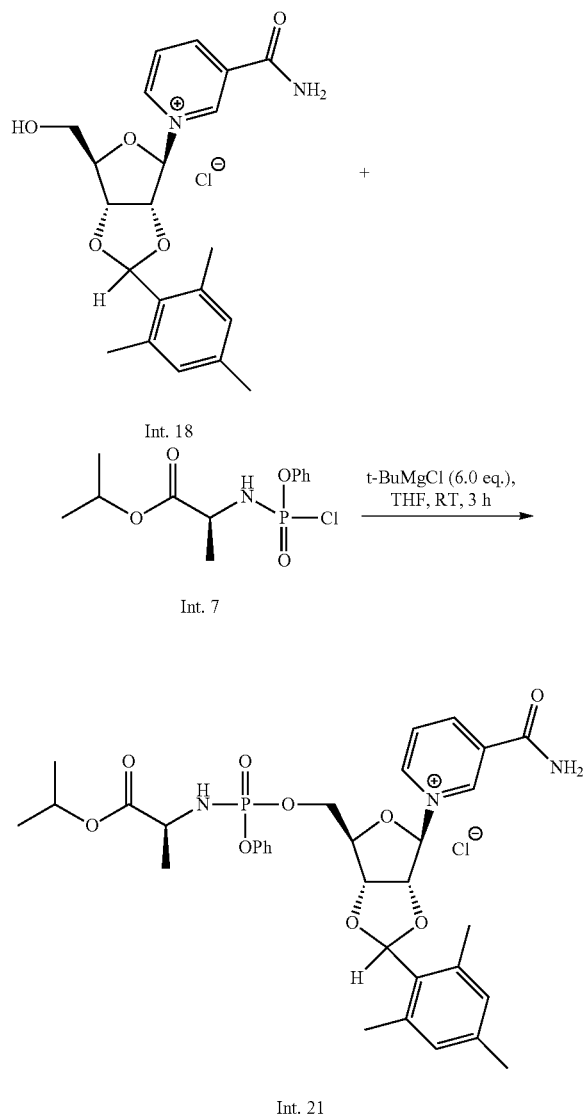

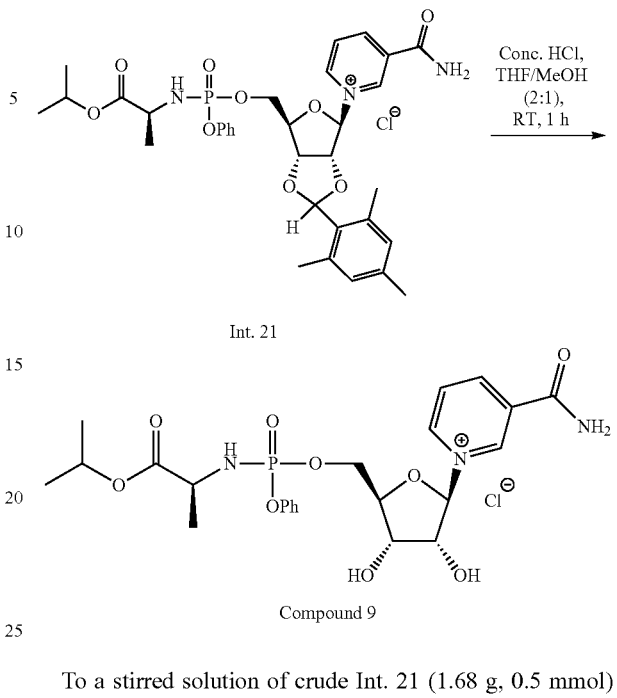

To a stirred suspension of Int. 18 (0.5 g, 1.29 mmol) in dry THF (20 mL) was added t-BuMgCl (7.8 mL, 7.8 mmol, 1.0 M in 2-MeTHF) dropwise over a period of 15 minutes at room temperature under Ar atmosphere. After 15 minutes, a solution of Int. 7 (1.2 g, 3.92 mmol) in dry THF (2 mL) was added dropwise. The resulting clear pale yellow solution was stirred for 3 h, then the excess base was quenched with MeOH (2 mL) at room temperature. The resulting mixture was concentrated under reduced pressure. The residue was purified by flash column chromatography (300 g of 100-200 silica gel, 20% MeOH-DCM) to afford Int. 21 (0.84 g) as a thick, pale yellow syrup, which was used in the next reaction without further purification.

LC-MS: m/z: 654.86 $[M]^+$ $R_f$=0.35 (Mobile phase: 20% MeOH-DCM).

To a stirred solution of crude Int. 21 (1.68 g, 0.5 mmol) in a mixture of THF/MeOH (2:1, 45 mL) was added conc. HCl (0.5 mL) at room temperature. The resulting mixture was stirred for 1 h, and the volatiles were removed under reduced pressure. The residue was purified by column chromatography (200 g of 100-200 silica gel, 20% MeOH-DCM) to afford Compound 9 (400 mg, 52.5% LCMS), which was further purified by Prep-HPLC to afford Compound 9 (29 mg, 2.13% yield over two steps) as a hygroscopic, white fluffy solid.

LC-MS: m/z: 524.73 $[M]^+$ $^1$H NMR (400 MHz, DMSO-$d_6$): δ 9.40 (s, 1H), 9.17 (d, J=6.4 Hz, 1H), 9.01 (d, J=8.0 Hz, 1H), 8.65 (brs, 1H, —NH), 8.28 (t, J=6.4 Hz, 1H), 8.22 (brs, 1H, —NH), 7.36-7.32 (m, 2H), 7.22-7.16 (m, 3H), 6.20-6.05 (m, 3H, -2OH), 5.74 (brs, 1H, —OH), 4.86-4.81 (m, 1H), 4.43-4.31 (m, 3H), 4.22-4.19 (m, 1H), 4.12 (brs, 1H), 3.85-3.77 (m, 1H), 1.21 (d, J=6.8 Hz, 3H), 1.14 (d, J=6.4 Hz, 6H).

Example 10: In Vitro Assays

Figure 2:
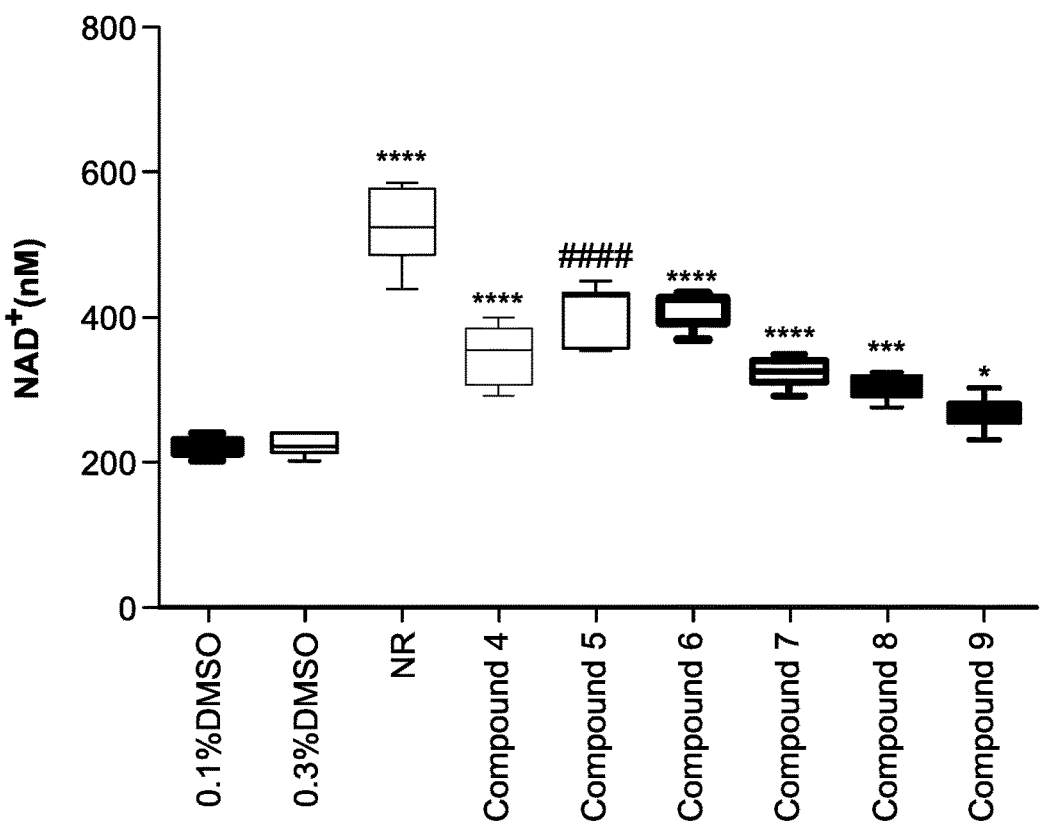
Figure 3:
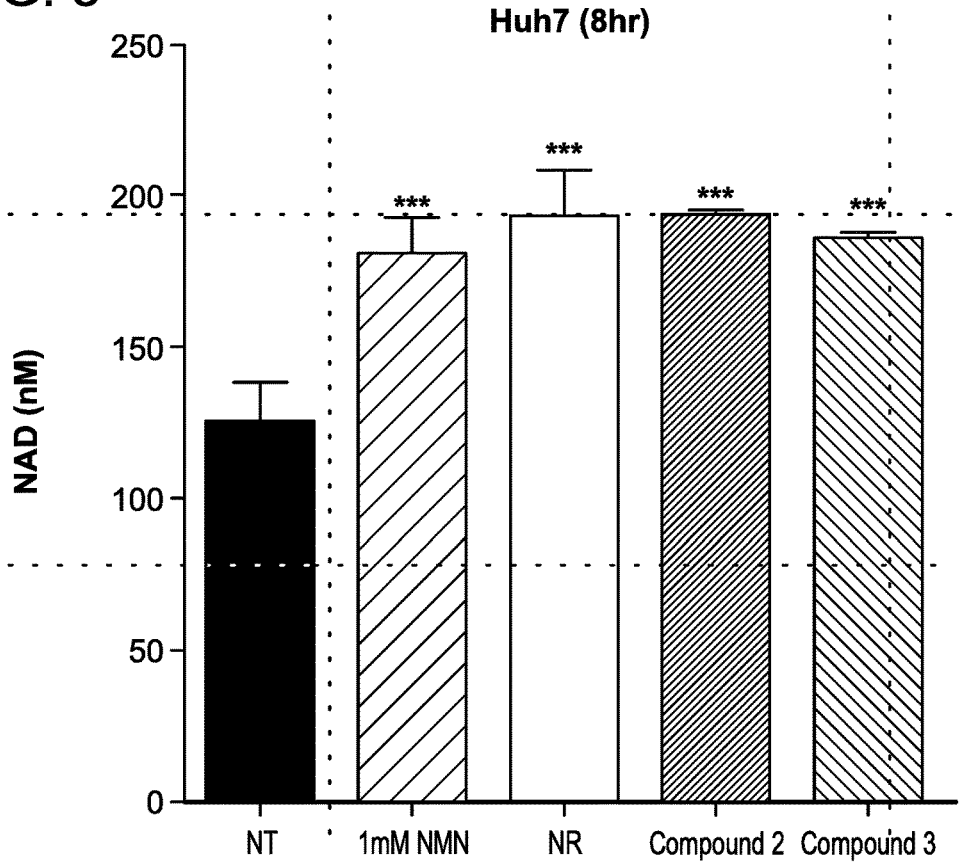
FIG. 3 is a bar graph showing certain compounds of the invention increase NAD$^+$ levels in Huh7 cells 8 hours post dose. See Example 10B.
Figure 4:
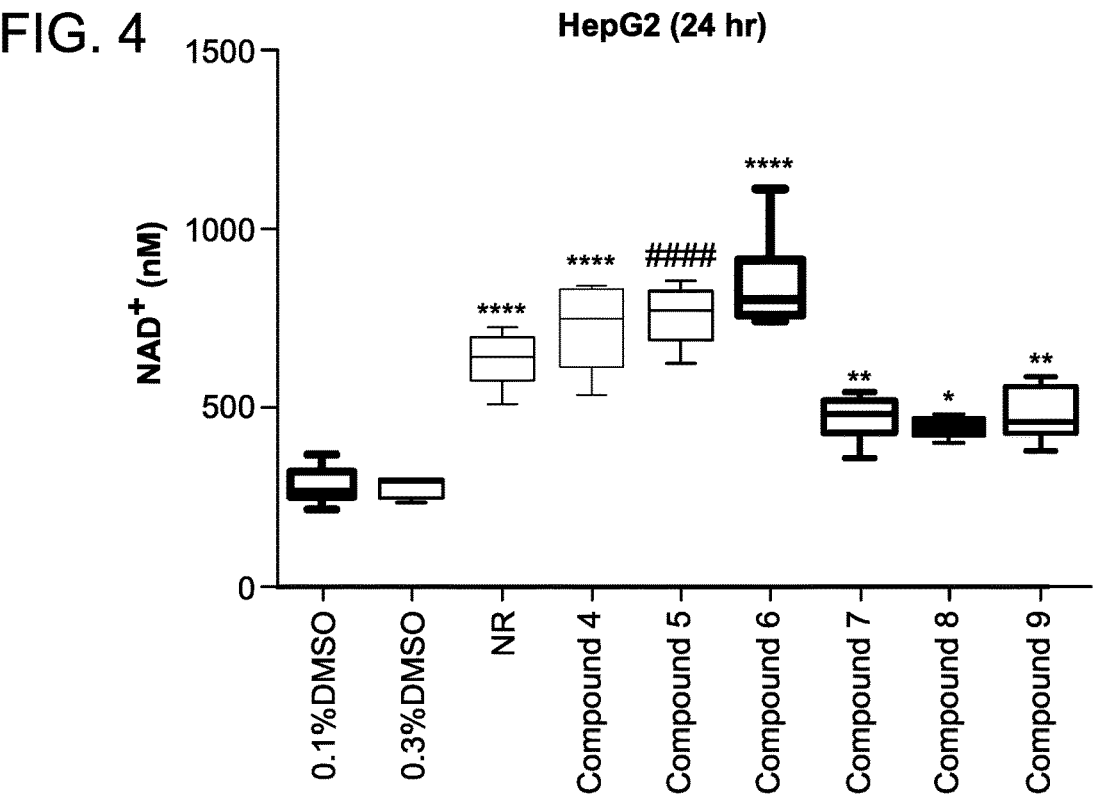
FIG. 4 is a bar graph showing certain compounds of the invention increase NAD$^+$ levels in HepG2 cells 24 hours post dose. See Example 10B.

Examples 10A and 10B describe in vitro assays for measuring NAD$^+$ concentration in various cell lines after treatment with the compounds of the invention. Example 10A describes measurement of NAD$^+$ concentration in general. Example 10B demonstrates an increase in NAD$^+$ concentration in mammalian AML12, Huh7, HepG2 cell lines after treatment with Compounds 2-9, as measured by an NADH/NAD$^+$ Glo Assay kit (results shown in FIGS. 1-4)

A. Measurement of NAD$^+$/NADH

NAD$^+$/NADH measurements were done using a modified version of manufacturer instructions supplied with the NAD$^+$/NADH Glo Assay (Promega). Cells were plated as done for proliferation assays and treated as indicated prior to preparation of cell extracts at various times after treatment. For extraction, cells were washed 3 times in ice-cold PBS, extracted in 100 µL ice-cold lysis buffer (1% dodecyltrimethylammonium bromide (DTAB) in 0.2 N NaOH or bicarbonate buffer (100 mM sodium carbonate, 20 mM sodium bicarbonate, 100 mM nicotinamide, 20 mM Triton X-100) diluted 1:1 with PBS), and either immediately assayed for frozen at −80° C. To measure NADH, 45 μL of sample was incubated at either 60° C. for 15 min or 75° C. for 30 min where basic conditions selectively degrade NAD+. To measure NAD+, 45 μL of the samples was moved to PCR tubes containing 22.5 μL 0.4 N HCl and incubated at 60° C. for 15 min, where acidic conditions selectively degrade NADH. Following incubations, samples were allowed to equilibrate to room temperature and then quenched by neutralizing with 45 μL of Tris/HCl (equal parts 0.5 M Trizma base and 0.4 N HCl (NADH) or 22.5 μL 0.5 M Tris base (NAD+). Manufacturer instructions were followed thereafter to measure NAD+/NADH. NAD+ concentration is back-calculated from a standard curve and normalized to total protein.

B. NAD+ Measurements in AML12, Huh7 and HepG2 Cell Lines Using NAD/NADH-Glo Assay Kit On Day 1, cells were plated onto uncoated, clear, 96-well TC plates at a density of 10,000 cells/well. On Day 0, cells were treated with appropriate dose of compound or DMSO with final DMSO concentration at 0.1% in all samples. At time point post-treatment, media was aspirated from cells and cells were washed once with 100 μL PBS. Cells were then lysed by adding 50 μL PBS and 50 μL 1% DTAB in a bicarbonate buffer and frozen at −80° C. At end of all time points, plates were thawed at room temperature with gentle shaking.

A standard curve of NAD+ was prepared in a 1:1 PBS:1% DTAB mixture and treated along with samples. An aliquot of 45 μL from each well was transferred to a new 96-well plate. 2.5 μL of 0.4N hydrochloric acid was added to each well. The plate was then incubated for 15 M at 60° C., then allowed to equilibrate to room temp for 15 minutes. 22.5 μL of 0.5M Trizma Base was added per well. 20 μL of this mixture is transferred to an opaque 384-well plate. The detection reagent was made as per the NAD/NADH-Glo Assay kit directions (Promega; Cat# G9071/9072) and 20 μL of this is added to each well of the 384-well plate.

The plate was incubated at room temperature for 1 hour then analyzed by reading the luminescence on a plate reader with a 500 ms integration time. The standard curve was plotted and fit with a 4-parameter best fit line. The samples were then interpolated from this best fit line to determine NAD+ concentration.

The results are shown in FIGS. 1-4, which demonstrate that the compounds disclosed therein increase NAD+ in AML12, Huh7 and HepG2 cells.

We claim:

1. A compound of Formula (I):

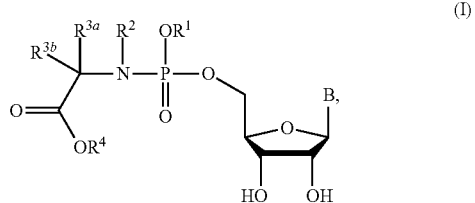

or a pharmaceutically acceptable salt thereof;

wherein:

B is

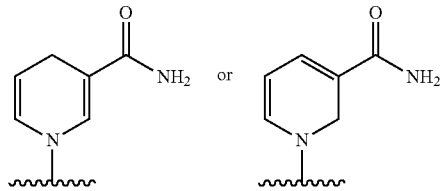 [SMILES: *N1C=CCC(C(N)=O)=C1 ; *N1C=CC=C(C(N)=O)C1]

$R^1$ is phenyl optionally substituted with one or more substituents selected from halogen, hydroxyl, nitro, cyano, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy, —N($R^{1a}$)$_2$, $C_1$-$C_6$-acylamino, —COR$^{1b}$, —OCOR$^{1b}$, —NHCOR$^{1b}$, —NHSO$_2$($C_1$-$C_6$-alkyl), —SO$_2$N($R^{1a}$)$_2$, and —SO$_2$($C_1$-$C_6$-alkyl), wherein each $R^{1a}$ is independently selected from hydrogen and $C_1$-$C_6$-alkyl, and $R^{1b}$ is hydroxyl, $C_1$-$C_6$-alkoxy, NH$_2$, NH($C_1$-$C_6$-alkyl), or N($C_1$-$C_6$-alkyl)$_2$;

$R^2$ is hydrogen or $C_1$-$C_6$-alkyl;

$R^{3a}$ and $R^{3b}$ are independently hydrogen, $C_1$-$C_6$-alkyl, $C_1$-$C_6$-alkoxy, benzyl, indolyl, or imidazolyl, wherein $C_1$-$C_6$-alkyl and $C_1$-$C_6$-alkoxy is optionally substituted with one or more of halogen, amino, amido, guanidyl, hydroxyl, thiol, or carboxyl, and benzyl is optionally substituted with one or more halogen or hydroxyl;

or $R^{3a}$ and $R^{3b}$ is taken together with the carbon atom to which they are attached to form a $C_3$-$C_6$ cycloalkyl group optionally substituted with one or more halogen, amino, amido, guanidyl, hydroxyl, thiol, and carboxyl; and $R^4$ is hydrogen, $C_1$-$C_6$-alkyl, $C_2$-$C_6$-alkenyl, $C_2$-$C_6$-alkynyl, or $C_3$-$C_6$-cycloalkyl.

2. The compound of claim 1, wherein the compound has the structure of formula (III):

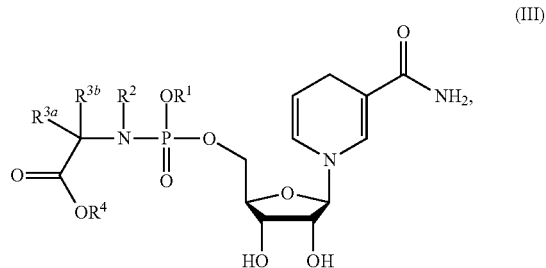

or a pharmaceutically acceptable salt thereof.

3. The compound of claim 1, wherein $R^1$ is unsubstituted phenyl.

4. The compound of claim 1, wherein $R^2$ is hydrogen.

5. The compound of claim 1, wherein one of $R^{3a}$ or $R^{3b}$ is hydrogen.

6. The compound of claim 5, wherein the compound has the structure of formula (IV):

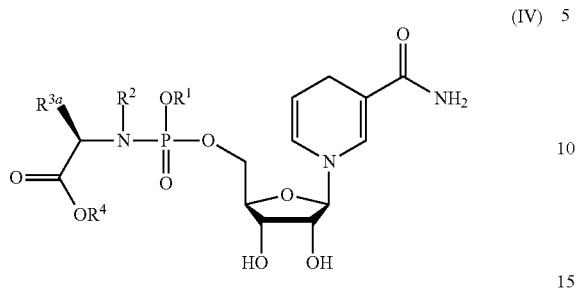

(IV)

or a pharmaceutically acceptable salt thereof.

7. The compound of claim 6, wherein $R^{3a}$ is optionally substituted $C_1$-$C_6$-alkyl.

8. The compound of claim 7, wherein $R^{3a}$ is unsubstituted $C_1$-$C_6$-alkyl.

9. The compound of claim 1, wherein $R^4$ is $C_1$-$C_6$-alkyl or $C_3$-$C_6$-cycloalkyl.

10. The compound of claim 9, wherein $R^4$ is methyl, isopropyl, or cyclohexyl.

11. The compound of claim 8, wherein $R^{3a}$ is methyl.

12. A pharmaceutical composition comprising a pharmaceutically acceptable carrier or excipient and the compound of claim 1, or a pharmaceutically acceptable salt thereof.

13. A method of treating a mitochondrial-related disease or condition in a subject, comprising administering to the subject in need thereof a therapeutically effective amount of one or more compounds of claim 1, or a pharmaceutically acceptable salt thereof.

14. The method of claim 13, wherein mitochondrial-related disease or condition is a muscle structure disorder, a neuronal activation disorder, a muscle fatigue disorder, a muscle mass disorder, a metabolic disease, a cancer, a vascular disease, an ocular vascular disease, a muscular eye disease, or a renal disease.

15. The method of claim 14, wherein:
the muscle structure disorder is selected from Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, or stress urinary incontinence;
the neuronal activation disorder is selected from amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder;
the muscle fatigue disorder is selected from chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, or thyrotoxic myopathy; the muscle mass disorder is cachexia, cartilage degeneration, cerebral palsy, compartment syndrome, critical illness myopathy, inclusion body myositis, muscular atrophy (disuse), sarcopenia, steroid myopathy, and systemic lupus erythematosus;
the beta oxidation disease is selected from systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of β-oxidation (RR-MADD);
the metabolic disease is selected from hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, Non-alcoholic fatty liver disease (NAFLD), Nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis;
the cancer is selected from colon cancer, cancer of the large intestine, skin cancer, breast cancer, prostate cancer, ovarian cancer, and lung cancer;
the vascular disease is selected from peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy;
the ocular vascular disease is selected from age-related macular degeneration (AMD), stargardt disease, hypertensive retinopathy, diabetic retinopathy, retinopathy, macular degeneration, retinal haemorrhage, and glaucoma;
the muscular eye disease is selected from strabismus, progressive external ophthalmoplegia, esotropia, exotropia, a disorder of refraction and accommodation, hypermetropia, myopia, astigmatism, anisometropia, presbyopia, a disorders of accommodation, and internal ophthalmoplegia; and
the renal disease is selected from glomerulonephritis, glomerulosclerosis, nephrotic syndrome, hypertensive nephrosclerosis, acute nephritis, recurrent hematuria, persistent hematuria, chronic nephritis, rapidly progressive nephritis, acute renal failure, chronic renal failure, diabetic nephropathy, and Bartter's syndrome.

16. The method of claim 13, wherein the mitochondrial-related disease or condition is selected from genetic lipodystrophy, non-alcoholic fatty liver disease (NAFLD), non-alcoholic steatohepatitis (NASH), renal ischemia/reperfusion injury (IRI), Duchenne & Becker muscular dystrophy, diabetes (type I or type II), obesity, and sarcopenia.

17. The method of claim 13, wherein the mitochondrial-related disease or condition is selected from Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, Pearson Syndrome, platinum-based chemotherapy induced ototoxicity, Cockayne syndrome, xeroderma pigmentosum A, Wallerian degeneration, and HIV-induced lipodystrophy.

* * * * *